(12) United States Patent
Luu et al.

(10) Patent No.: US 9,237,831 B1
(45) Date of Patent: Jan. 19, 2016

(54) WATER SOLUBLE SHEET SOAP IN A WATERLESS PUMP BOTTLE, READY TO MAKE A FOAM CLEANSER BY ADDING WATER

(71) Applicant: Georgia-Pacific Consumer Products LP, Atlanta, GA (US)

(72) Inventors: Phuong Van Luu, Appleton, WI (US); Chiehlung Jay Hsu, Alpharetta, GA (US); Bruce J. Kokko, Neenah, WI (US); Sarah A. Lemke, Appleton, WI (US); Taiye Phillips Oriaran, Appleton, WI (US); David W. White, Clintonville, WI (US)

(73) Assignee: Georgia-Pacific Consumer Products LP, Atlanta, GA (US)

( * ) Notice: Subject to any disclaimer, the term of this patent is extended or adjusted under 35 U.S.C. 154(b) by 0 days.

(21) Appl. No.: 14/446,877

(22) Filed: Jul. 30, 2014

Related U.S. Application Data

(60) Provisional application No. 61/868,701, filed on Aug. 22, 2013.

(51) Int. Cl.
| | | |
|---|---|---|
| *A47K 5/16* | (2006.01) | |
| *A47K 5/12* | (2006.01) | |
| *A47K 10/16* | (2006.01) | |
| *A47K 10/32* | (2006.01) | |
| *B05B 11/00* | (2006.01) | |

(Continued)

(52) U.S. Cl.
CPC .................. *A47K 5/16* (2013.01); *A47K 5/1217* (2013.01); *A47K 10/16* (2013.01); *A47K 5/12* (2013.01); *A47K 10/32* (2013.01); *A47K 10/3818* (2013.01); *A47K 2010/328* (2013.01);

*A61K 8/046* (2013.01); *B05B 7/0037* (2013.01); *B05B 11/0005* (2013.01); *B05B 11/3042* (2013.01)

(58) Field of Classification Search
CPC ........... A47K 5/12; A47K 5/16; A47K 10/16; A47K 10/32; A47K 10/3818; A47K 2010/328; A47K 5/1217; A61K 8/046; B05B 7/0037; B05B 11/0005; B05B 11/3042
See application file for complete search history.

(56) References Cited

U.S. PATENT DOCUMENTS

| 2,746,798 | A | * | 5/1956 | Wardell, Jr. .................. 239/274 |
|---|---|---|---|---|
| 4,027,789 | A | | 6/1977 | Dickey |

(Continued)

FOREIGN PATENT DOCUMENTS

| CN | 1357613 A | 7/2002 |
|---|---|---|
| EP | 2537510 A | 12/2012 |

(Continued)

OTHER PUBLICATIONS

Maguire et al., "Exploring two-dimensional soap-foam films using fullerene (C60) nanosensors", 2003 American Institute of Physics, Applied Physics Letters, vol. 82, No. 16, Apr. 21, 2003, pp. 2592-2594.

(Continued)

*Primary Examiner* — Frederick C Nicolas
(74) *Attorney, Agent, or Firm* — Laura L. Bozek

(57) ABSTRACT

The present invention is directed to a foam soap delivery system. In accordance with the present invention, the system includes a paperboard core with a plurality of sheets of paper or tissue wound around the paperboard core. A dispenser is removably disposed within the paperboard core, and a water-soluble sheet soap is disposed within the dispenser.

68 Claims, 4 Drawing Sheets

(51) Int. Cl.
 A47K 10/38 (2006.01)
 A61K 8/04 (2006.01)
 B05B 7/00 (2006.01)

(56) References Cited

U.S. PATENT DOCUMENTS

| | | | |
|---|---|---|---|
| 4,436,224 A * | 3/1984 | McInerny | 222/183 |
| 5,037,006 A | 8/1991 | Kock | |
| 5,062,986 A | 11/1991 | Fujita et al. | |
| 5,671,872 A * | 9/1997 | Daniels, Jr. | 222/192 |
| 5,819,989 A * | 10/1998 | Saraceni | 222/192 |
| 5,906,299 A | 5/1999 | Hagleitner | |
| 5,984,146 A | 11/1999 | Kaufman | |
| 6,138,874 A * | 10/2000 | Audrey | 222/192 |
| 6,177,391 B1 | 1/2001 | Zafar | |
| 6,516,976 B2 | 2/2003 | Lewis et al. | |
| 6,708,826 B1 | 3/2004 | Ginsberg et al. | |
| 6,840,408 B1 | 1/2005 | Foster et al. | |
| 6,923,346 B2 | 8/2005 | Foster et al. | |
| 7,285,520 B2 | 10/2007 | Krzysik et al. | |
| 7,357,255 B2 | 4/2008 | Ginsberg et al. | |
| 7,364,053 B2 | 4/2008 | Ophardt | |
| 7,434,692 B2 | 10/2008 | Ginsberg et al. | |
| 7,592,049 B2 | 9/2009 | Jones et al. | |
| 7,631,764 B2 | 12/2009 | Ginsberg et al. | |
| 7,638,475 B2 | 12/2009 | Dwiggins et al. | |
| 7,819,289 B2 | 10/2010 | Willis | |
| 8,197,830 B2 | 6/2012 | Helfman et al. | |
| 8,479,957 B2 * | 7/2013 | Ophardt | 222/192 |
| 2002/0098994 A1 | 7/2002 | Zafar | |
| 2004/0029762 A1 | 2/2004 | Hensley | |
| 2005/0008576 A1 | 1/2005 | Makansi | |
| 2006/0002987 A1 | 1/2006 | Bevacqua et al. | |
| 2006/0228319 A1 | 10/2006 | Vona, Jr. et al. | |
| 2007/0241121 A1 | 10/2007 | Bolich et al. | |
| 2009/0194563 A1 | 8/2009 | Lewis et al. | |
| 2009/0286706 A1 | 11/2009 | Chakrabarty et al. | |
| 2010/0150976 A1 | 6/2010 | Schnitzler et al. | |
| 2010/0204341 A1 | 8/2010 | Yu et al. | |
| 2010/0247459 A1 | 9/2010 | Drovetskaya et al. | |
| 2010/0278886 A1 | 11/2010 | Yu et al. | |
| 2010/0285604 A1 | 11/2010 | Jurman et al. | |
| 2011/0095051 A1 | 4/2011 | Liao et al. | |
| 2014/0135245 A1 | 5/2014 | Annaheim et al. | |

FOREIGN PATENT DOCUMENTS

JP 2003073700 3/2003
KR 930000782 B1 2/1993

OTHER PUBLICATIONS

Ashland; "Benecel Hydroxypropyl Methylcellulose for Personal Care"; Ashland Inc.; p. 1-28; 2010-2013.

\* cited by examiner

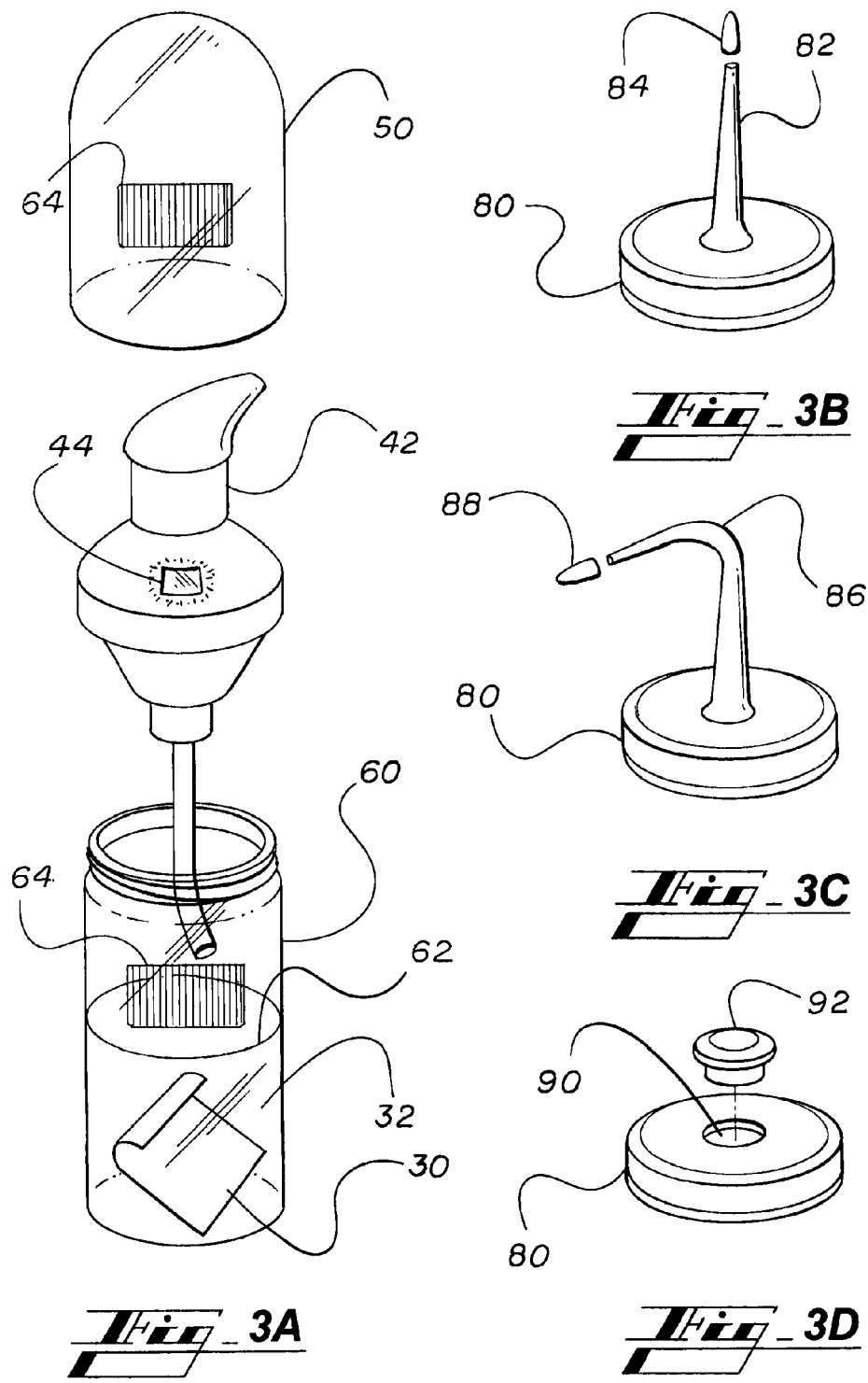

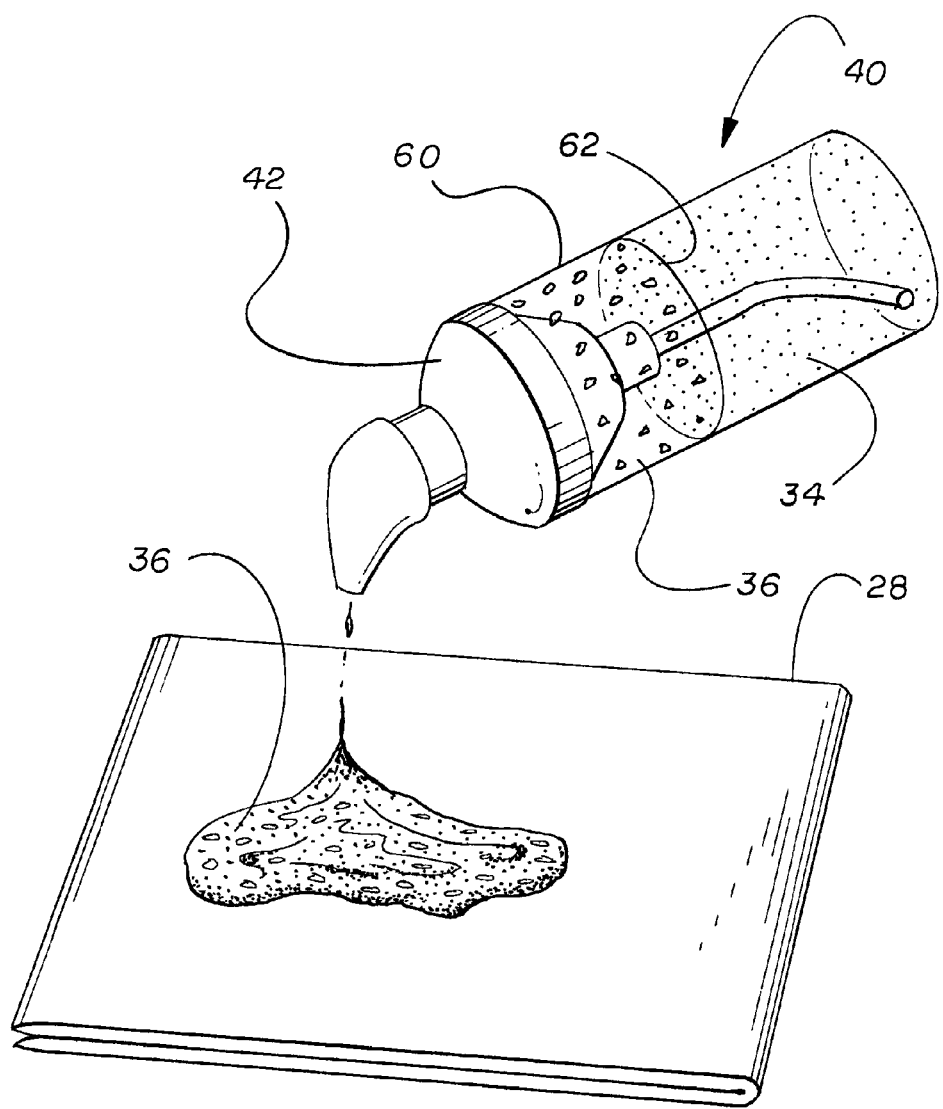
Fig_4

WATER SOLUBLE SHEET SOAP IN A WATERLESS PUMP BOTTLE, READY TO MAKE A FOAM CLEANSER BY ADDING WATER

CROSS REFERENCE TO RELATED APPLICATION

This application is based on U.S. Provisional Patent Application No. 61/868,701 filed Aug. 22, 2013, which is incorporated herein by reference in its entirety.

TECHNICAL FIELD

The present invention is directed generally to foam soap delivery systems. More specifically, the present invention is related to a water-soluble sheet soap packaged within a dispenser.

BACKGROUND OF THE INVENTION

Proper hygiene aides in preventing the transmission of bacteria, viruses, soils, and other contaminants. Frequent use of hand soaps, shampoos, body washes, facial cleansers, shave foams, makeup removers, and the like help to maintain personal hygiene. Conventional product forms for personal cleansing include, among others, bars, liquids, gels, foams, and powders.

Conventional products have disadvantages. For example, bar soaps are inconvenient for travel because they must be dried or stored in a portable case. Aerosols are restricted from airplanes, and liquid soap containers are cumbersome and can leak. Further, liquids are subject to postal restrictions. Finally, conventional liquid soaps have limited shelf-lives, which begin at the time of production and can expire long before a consumer uses the product.

Frequently, dispensing appropriate amounts from these product forms is not predictable without repeated use and experimentation. Often a consumer misgauges and over-dispenses, resulting in product waste. In contrast, dispensing an insufficient amount of soap can be ineffective.

Based on the foregoing, there still exists a need for a soap product that is lightweight, can dispense a metered amount of a personal cleansing product, is not susceptible to leakage during travel or shipment, and is not limited by shelf-life. Accordingly, it is to solving this and other needs the present invention is directed.

SUMMARY OF THE INVENTION

The present invention is directed to a foam soap delivery system. In accordance with the present invention, the system includes a paperboard core with a plurality of sheets of paper or tissue wound around the paperboard core. The paperboard core has a first distal end and a second distal end. A dispenser is removably disposed within the paperboard core, and a water-soluble sheet soap is disposed within the dispenser. The sheet soap is dissolvable in water to form a foamable solution and has a bending resistance in a range between about 1 milligram-force (mgf) and about 50 mgf as measured by Technical Association of the Pulp and Paper Industry (TAPPI) test method T 543 om-11. The sheet soap includes a contact product of polyvinyl alcohol, at least one film-forming material, an ionic cross-linker composition, and a surfactant composition. The polyvinyl alcohol, the at least one film-forming material, and the ionic cross-linker composition define a film-forming composition. The film-forming composition is present in a range between about 20% and about 50% by weight of the total weight of the sheet soap. The polyvinyl alcohol is present in the film-forming composition in a range between about 5% and about 60% by weight of the total weight of the sheet soap, and the ionic cross-linker composition is present in the film-forming composition in a range between about 1% and about 10% by weight of the total weight of the sheet soap. The dispenser discharges a foam upon stimulation by a user when water is present within the dispenser.

In one aspect, the dispenser comprises a container and a pump removably and sealably engaging the container. The pump can be a hand-actuatable pump. In another aspect, the sheet soap is dissolvable in the water to produce a foamable solution, and the hand-actuatable pump mixes air with the foamable solution to produce and discharge the foam upon actuation by the user. The pump can be a motion-actuated pump with a sensor which detects a motion of the user. Upon detecting the motion, the pump mixes air with the foamable solution to produce and discharge the foam. Yet, in another aspect, the dispenser includes a container and a cap removably and sealably engaging the container. The cap can include a nozzle, a spout, or an outlet. Still yet, in another aspect, a hanger is disposed on the dispenser. The hanger can have at least one hook extending outwardly in either a radial or an axial direction with respect to the hanger. Further, the hanger can engage one of the distal ends of the paperboard core.

In one aspect, the surfactant composition of the water-soluble sheet soap is present in a range between about 40% and about 50% by weight of the total weight of the sheet soap. In another aspect, the surfactant composition comprises a nonionic surfactant, an anionic surfactant, a cationic surfactant, an amphoteric surfactant, or any combination thereof. Optionally, the sheet soap includes a filler. In one aspect, the filler is present in a range between about 1% and about 2% by weight of the total weight of the sheet soap.

Yet, in another aspect, a foam soap delivery system includes a paperboard core with a plurality of sheets of paper or tissue wound around the paperboard core. The paperboard core has a first distal end and a second distal end. A dispenser is removably disposed within the paperboard core, and a water-soluble sheet soap is disposed within the dispenser. The sheet soap is dissolvable in water to form a foamable solution and has a bending resistance in a range between about 1 mgf and about 50 mgf as measured by TAPPI test method T 543 om-11. The sheet soap includes a contact product of polyvinyl alcohol, at least one film-forming material, an ionic cross-linker composition, a surfactant composition, and an antimicrobial composition. The polyvinyl alcohol, the at least one film-forming material, and the ionic cross-linker composition define a film-forming composition. The film-forming composition is present in a range between about 10% and about 40% by weight of the total weight of the sheet soap. The polyvinyl alcohol is present in the film-forming composition in a range between about 10% and about 55% by weight of the total weight of the sheet soap, and the ionic cross-linker composition is present in the film-forming composition in a range between about 1% and about 10% by weight of the total weight of the sheet soap. The dispenser discharges a foam upon stimulation by a user when water is present within the dispenser.

The surfactant composition of the water-soluble sheet soap can be present in a range between about 40% and about 60% by weight of the total weight of the sheet soap. The antimicrobial composition can include a natural antimicrobial of vegetal or animal origin. In another aspect, the antimicrobial can be present in a range between about 1% to about 5% by weight of the total weight of the sheet soap. Optionally, the water-soluble sheet soap includes an emollient in a range between about 1% and about 5% by weight of the total weight of the sheet soap.

Still yet, in another aspect, the foam soap delivery system includes a paperboard core with a plurality of sheets of paper or tissue wound around the paperboard core. The paperboard core has a first distal end and a second distal end. A dispenser is removably disposed within the paperboard core, and a water-soluble sheet soap disposed within the dispenser. The sheet soap is dissolvable in water to form a foamable solution and has a bending resistance in a range between about 1 mgf and about 50 mgf as measured by TAPPI test method T 543 om-11. The sheet soap includes a contact product of polyvinyl alcohol, at least one film-forming material, an ionic cross-linker composition, and a surfactant composition. The polyvinyl alcohol, the at least one film-forming material, and the ionic cross-linker composition define a film-forming composition. The film-forming composition is present in a range between about 20% and about 50% by weight of the total weight of the sheet soap. The polyvinyl alcohol is present in the film-forming composition in a range between about 5% and about 60% by weight of the total weight of the sheet soap, and the ionic cross-linker composition is present in the film-forming composition in a range between about 1% and about 10% by weight of the total weight of the sheet soap. The surfactant composition is present in a range between about 50% and about 60% by weight of the total weight of the sheet soap. The dispenser discharges a foam upon stimulation by a user when water is present within the dispenser.

In one aspect, a foam soap delivery system dispenses a metered amount of foam. The system includes a paperboard core with a plurality of sheets of paper or tissue wound around the paperboard core. The paperboard core has a first distal end and a second distal end. A dispenser is removably disposed within the paperboard core, and a water-soluble sheet soap disposed within the dispenser. The sheet soap is dissolvable in water to form a foamable solution and has a bending resistance in a range between about 1 mgf and about 50 mgf as measured by TAPPI test method T 543 om-11. The sheet soap includes a contact product of polyvinyl alcohol, at least one film-forming material, an ionic cross-linker composition, and a surfactant composition. The polyvinyl alcohol, the at least one film-forming material, and the ionic cross-linker composition define a film-forming composition. The film-forming composition is present in a range between about 20% and about 50% by weight of the total weight of the sheet soap. The polyvinyl alcohol is present in the film-forming composition in a range between about 5% and about 60% by weight of the total weight of the sheet soap, and the ionic cross-linker composition is present in the film-forming composition in a range between about 1% and about 10% by weight of the total weight of the sheet soap. The dispenser discharges a metered amount of foam upon stimulation by a user when sufficient water is present within the dispenser to produce an effective concentration of the foamable solution. The effective concentration of the foamable solution is defined as at least one milligram of sheet soap per milliliter of water.

It is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods, and systems for carrying out the present invention. It is important, therefore, that the claims be regarded as including such equivalent constructions insofar as they do not depart from the spirit and scope of the present invention.

Other advantages and capabilities of the invention will become apparent from the following description taken in conjunction with the examples showing aspects of the present invention.

BRIEF DESCRIPTION OF THE DRAWINGS

The invention will be better understood and the above object as well as objects other than those set forth above will become apparent when consideration is given to the following detailed description thereof. Such description makes reference to the annexed drawings wherein:

FIG. 3A is an elevation, exploded view of a dispenser;

FIG. 3B is an elevation view of a cap with a nozzle;

FIG. 3C is an elevation view of a cap with a spout;

FIG. 3D is an elevation view of cap with an outlet; and

FIG. 4 is an isometric perspective view of a dispenser discharging a foam onto a sheet of paper or tissue.

DETAILED DESCRIPTION OF THE INVENTION

Figure 1:
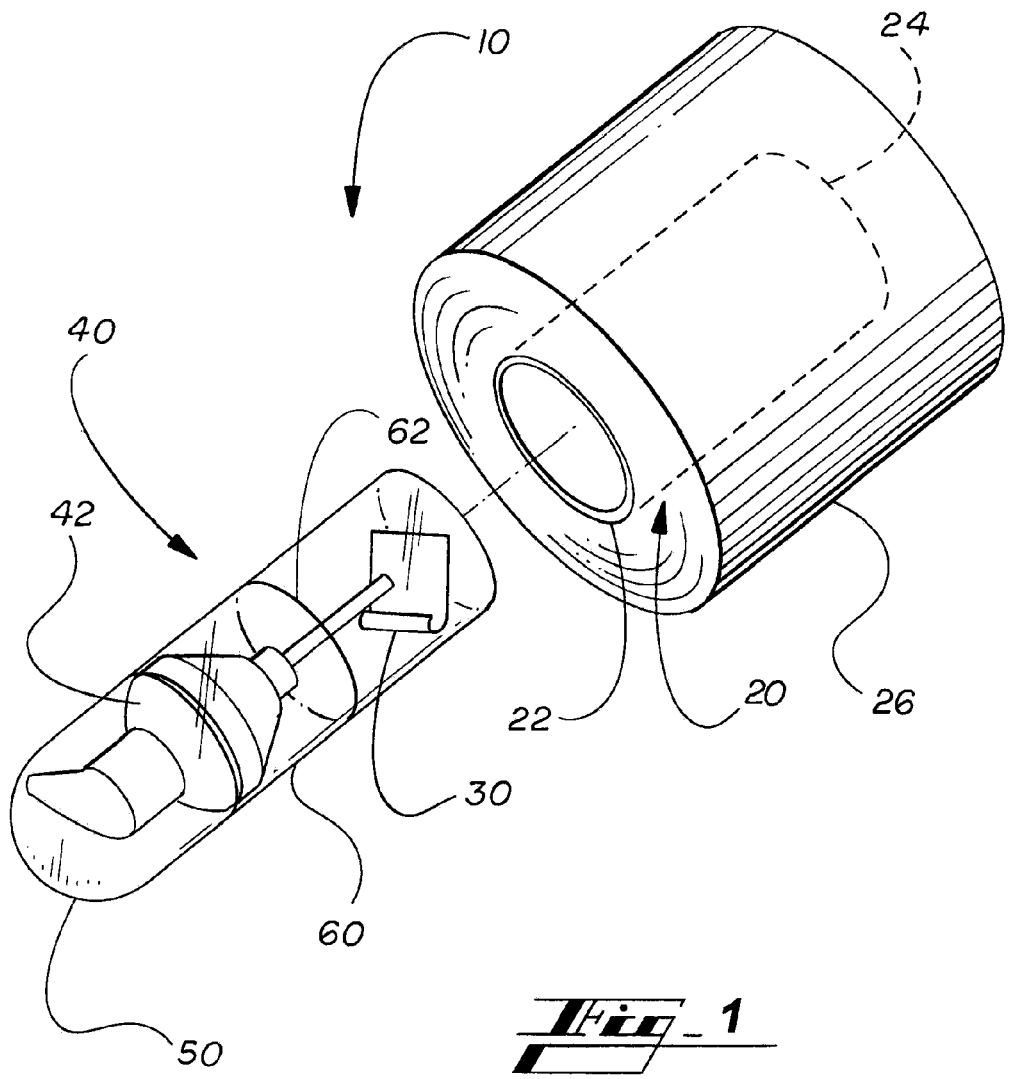
FIG. 1 is an isometric perspective view of a dispenser as it is removed from its associated roll of paper or tissue.

For a fuller understanding of the nature and desired objects of this invention, reference should be made to the above and following detailed description taken in connection with the accompanying figures. When reference is made to the figures, like reference numerals designate corresponding parts throughout the several figures.

The term "personal hygiene cleanser" as used herein includes any composition that is applied and distributed on the skin and/or hair to remove dirt, remove oil, provide lubricity, and/or soften hair. In addition, a personal hygiene cleanser includes one or more surfactants that dissolve in water at room temperature and is applied to skin and/or hair. In particular, a personal hygiene cleanser includes, but is not limited to, a hand soap, a shampoo, a facial cleanser, a body wash, a shave foam, a makeup remover, or any combination thereof.

The term "surfactant," as used herein, includes any substance that reduces the interfacial tension between two immiscible substances and/or solubilizes oils. The surfactants can be amphoteric, anionic, cationic, nonionic, or any combination thereof.

The terms "water-soluble," "water solubility," "dissolves in water," variations thereof, and similar terms, refer to physical characteristics of a substance, in which the substance breaks apart or combines with water to form a solution when water is added. The terms "water-insoluble," "water insolubility," variations thereof, and similar terms refer to physical characteristics of a substance, in which the substance does not break apart or combine with water to form a solution when water is added.

The terms "sheet soap," "soap film," "paper soap," variations thereof, and similar terms, can be used to signify a soap which is water-soluble and applied to skin and/or hair. Sheet soaps remove dirt and/or oil, provide lubricity, and/or soften hair.

The terms "by weight" and "% by weight," as used herein refer to weight of a given substance divided by the total weight of the sheet soap, including all components. Typically, weight is measured in grams. For example, a composition with a total weight of 100 grams, which includes 25 grams of substance A, will include substance A in 25% by weight.

The term "foamable solution," as used herein, refers to a solution that can generate a foam. The solution includes a sheet soap dissolved in water, or an aqueous solution. The term "foam," as used herein, refers to a mass of bubbles of air or gas in a matrix of liquid, such as water or other aqueous solution.

The Foam Soap Delivery System

FIG. 1 illustrates an isometric perspective view of a foam soap delivery system 10 made in accordance with the present invention. The system includes a paperboard core 20 with a plurality of sheets of paper or tissue 26 wound around the paperboard core 20. Alternatively, the paperboard core 20 can be substituted with a polymeric core. The paperboard core 20 has a first distal end 22 and a second distal end 24. A dispenser 40 is removably disposed within the paperboard core 20, and a water-soluble sheet soap 30 is disposed within the dispenser 40. In one aspect, the dispenser 40 includes a container 60 and a pump 42 removably and sealably engaging the container 60. The container 60 can include a water-fill line 62 to enable the consumer or user to easily gauge the appropriate volume of water necessary to provide an effective concentration of the water-soluble sheet soap 30. Optionally, the dispenser 40 includes a lid 50 to assist in preventing leakage from the pump 42.

In one aspect, the diameter of the paperboard core 20 is in a range between about 1.5 inches and about 1.75 inches. In another aspect, the length of the paperboard core 20 is between about 1.5 inches and about 12 inches. The plurality of sheets of paper or tissue 26 can be any paper or tissue product. Examples of suitable papers or tissues include, but are not limited to, toilet papers, paper towels, tissues, baby wipers, napkins, wet wipes, or variations thereof. The plurality of sheets of paper or tissue 26 can be made of natural fibers, synthetic fibers, or combinations thereof. The plurality of sheets of paper or tissue 26 can be a continuous sheet. Accordingly, the user can tear a sheet of any desired size from the roll. The continuous sheet can also include perforations or indentions for easy tearing.

Figure 2:
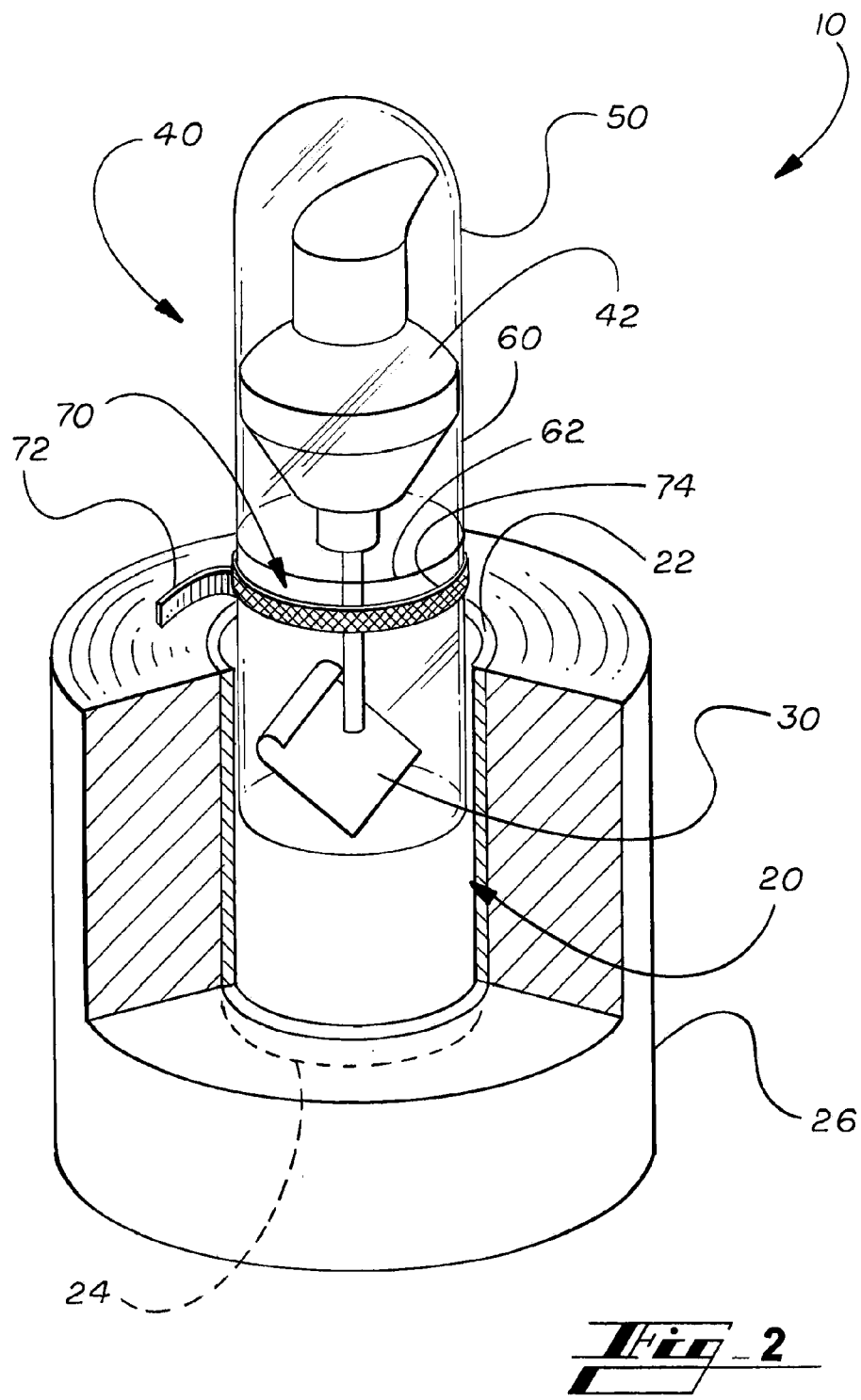
FIG. 2 is a partial isometric cross-section view of a dispenser partially disposed within a roll of paper or tissue.

Referring to FIG. 2, the foam soap delivery system 10 includes a paperboard core 20 with a plurality of sheets of paper or tissue 26 wound around the paperboard core 20. The dispenser 40 includes a hanger 70 disposed on the dispenser 40. The dispenser 40 is removably disposed within the paperboard core 20, and the water-soluble sheet soap 30 is disposed within the dispenser 40. The dispenser 40 includes a container 60 and a pump 42 removably and sealably engaging the container 60. The container 60 includes a water-fill line 62. The dispenser 40 includes a lid 50 to assist in preventing leakage from the pump 42. The hanger 70 can include a ring 74 and at least one hook 72 extending outwardly in either a radial or axial direction with respect to the hanger 70. When the dispenser 40 is disposed within the paperboard core 20, the at least one hook 72 engages one of the distal ends 22 (as shown in FIG. 2) or 24 (not shown) of the paperboard core 20. Thus, the hanger 70 secures the dispenser 40 to the paperboard core 20 at a position with respect to the paperboard core 20 to provide easy access and extraction capability of the dispenser 40 from the paperboard core 20, thereby providing a convenient, portable personal cleaning system.

The Hanger

The hanger 70 can be attached to the dispenser 40 during manufacture. The hanger 70 can be a permanent or removable fixture on the dispenser 40. Alternatively, the hanger 70 can be removably placed on the dispenser 40 by the user as needed. For example, the user can remove the hanger 70 to use the system 10 at home or work. When the system 10 is used during travel, the user can place the hanger 70 on the dispenser 40 to secure the dispenser 40 to the paperboard core 20, providing in a single unit.

In another aspect, the hanger 70 comprises a clamp (not shown) that attaches to the dispenser. The width of the hanger 70 comprising a ring 74 or clamp can be appropriately tailored as desired. In one aspect, the width of the hanger 70 is in a range between about 0.1 inch and about 3 inches. Non-limiting examples of materials which can be used to form the hanger 70 include paperboard and plastic.

The at least one hook 72 can be any type that secures the dispenser to one of the distal ends of the paperboard core 22 or 24. Examples of hooks 72 include, but are not limited to, pegs, nails, knobs, catches, fishhooks, fasteners, clasps, clips, or buttons. Yet, in another aspect, the hook 72 is attached directly to the dispenser 40 without a ring 74 or clamp. Examples of suitable materials for the hanger 70 or hook 72 include, but are not limited to, plastics, such as synthetic and semi-synthetic polymers, metals, such as metal alloys, and combinations thereof.

The Dispenser

Referring to FIGS. 3A, 3B, 3C, and 3D, the dispenser 40 (see FIG. 1) comprises a container 60, a pump 42, and a lid 50. The container 60 includes a water-fill line 62. The sheet soap 30 is disposed within the container 60. Optionally, refill sheet soaps 30 can be attached to the exterior of either the container 60 or the lid 50 in a separate refill pocket 64. The refill sheet soaps 30 in the refill pocket 64 can be wrapped in a water-degradable or non-water-degradable film. The size, shape, and position of the separate refill pocket 64 is not intended to be limited and can vary depending on the desired use. Any type of pump 42 that can removably and sealably engage the container 60 can be used. As discussed above, the sheet soap 30 is dissolvable in water 32, which is added to the container 60 by the user, to produce a foamable solution 34 (see FIG. 4). The pump 42 can mix air with the foamable solution 34 to produce a foam 36 (see FIG. 4). The pump 42 can be a hand actuatable pump that mixes air with the foamable solution to discharge the foam 36 upon actuation by the user. In addition, the pump 42 can be a motion-actuated pump having a sensor 44 which detects motion of the user. Upon sensing motion of the user, the pump 42 can mix air with the foamable solution 34 to produce and discharge the foam 36. Optionally, the pump 42 includes lid 50, as discussed above. Further, the dispenser 40 can include any cap 80 that removably and sealably engages the container 60. As illustrated in FIGS. 3B, 3C, and 3D, the cap 80 can include a nozzle 82 with a nozzle top 84 (FIG. 3B), a spout 86 with a spout top 88 (FIG. 3C), or an outlet 90 with an outlet plug 92 (FIG. 3D).

FIG. 4 (with reference to FIG. 3A) is an illustration of the dispenser 40 discharging foam 36 onto the paper or tissue 28. The container 60 includes a water-fill line 62. After water 32 is added to the container 60, the sheet soap 30 dissolves to form the foamable solution 34 within the dispenser 40. In one aspect, both the foamable solution 34 and foam 36 are disposed within the container 60 of the dispenser 40, and the pump 42 is a hand-actuatable pump. Upon stimulation by the user, the pump 42 discharges the foam 36 onto the paper or tissue 28.

The size, shape, and type of dispenser 40 are selected to fit the user's needs. For example, a small hand-actuatable pump dispenser can be appropriate to carry in a bag or purse. Alternatively, an automatic pump dispenser can be convenient for a public restroom. The dispenser can have any diameter that fits within the paperboard core 20 of a paper or tissue product. In one aspect, the diameter of the dispenser 40 is in a range between about 1 inch and 1.7 inch. In another aspect, the diameter of the dispenser 40 is in a range between about 1.2 inch and 1.6 inch. Yet, in another aspect, the diameter of the dispenser 40 is in a range between about 1.3 inch and 1.8 inch.

Examples of manually actuated dispensers which can be employed in the present invention include those disclosed in U.S. Pat. Nos. 6,840,408; 6,923,346; 5,037,006; 4,027,789; 5,984,146; 5,906,299; and U.S. Patent Appl. Publication No. 2009/0194563, each of which is incorporated herein in its entirety by reference. Further, examples of automatic dispensers employable in the present invention include those disclosed in U.S. Patent Appl. Publication No. 2011/0095051; and U.S. Pat. No. 7,364,053, each of which is incorporated herein in its entirety by reference. It is to be noted that the foregoing examples are non-limiting, and any dispenser that can discharge a foam can be used in the present invention.

The Sheet Soap

The sheet soap 30 comprises a contact product of a polyvinyl alcohol, at least one film-forming material, an ionic cross-linker composition, and a surfactant composition. The polyvinyl alcohol, the at least one film-forming material, and the ionic cross-linker composition define a film-forming composition. The film-forming composition is present in a range between about 10% and about 50% by weight of the total weight of the sheet soap. In one aspect, the film-forming composition is present in a range between about 20% and about 50% by weight of the total weight of the sheet soap. In another aspect, the film-forming composition is present in a range between about 10% and about 40% by weight of the total weight of the sheet soap. Yet, in another aspect, the film-forming composition is present in a range between about 20% and about 40% by weight of the total weight of the sheet soap. Still yet, in another aspect, the film-forming composition is present in about or in any range between about 5%, 10%, 15%, 20%, 25%, 30%, 35%, 40%, 45%, 50%, and 55% by weight of the total weight of the sheet soap.

Polyvinyl Alcohol

In one aspect, the polyvinyl alcohol is present in the film-forming composition in a range between about 5% and about 60% by weight of the total weight of the sheet soap. In another aspect, the polyvinyl alcohol is present in the film-forming composition in a range between about between about 10% and about 55% by weight of the total weight of the sheet soap. Yet, in another aspect, the polyvinyl alcohol is present in the film-forming composition in a range between about between about 15% and about 50% by weight of the total weight of the sheet soap. Still yet, in another aspect, the polyvinyl alcohol is present in the film-forming composition about or in any range between about 5%, 10%, 15%, 20%, 25%, 30%, 35%, 40%, 45%, 50%, 55%, and 60% by weight of the total weight of the sheet soap.

Film-Forming Material

Examples of film-forming materials include synthetic, natural, or modified polymers. Suitable film-forming materials include, but are not limited to, vinyl polymers, such as 2-pyrrolidinone-1-ethenyl homopolymer (also called polyvinyl pyrrolidone); polyvinyl pyrrolidone blends (sold as DISINTEX 75 and VIVIPRINT PS-10 by Ashland, Inc., Covington, Ky.); or blends polyvinyl pyrrolidone, with urea and cellulose (sold as DISINTEX 600 by Ashland, Inc.); cellulose-based polymers, such as hydroxypropyl cellulose (sold as KLUCELL by Ashland, Inc.); (hydroxypropylcellulose) polyethylene glycol; hydroxypropylmethyl cellulose (HPMC) (sold as BENECAL hydroxypropylmethyl cellulose by Ashland, Inc.); hydroxyethyl cellulose; hydroxypropyl cellulose gelatin; or carboxymethyl cellulose; starches, such as modified starch; natural starch; nano starch; hydroxypropyl starch phosphate; aluminum starch octenyl succinate; hydroxypropylated high amylose starch; gums and gum derivatives, such as xantham gum; guar gum; locust bean gum; karaya gum; tragacanth gum; *acacia* gum; or arabic gum; polysaccharides, such as amylase; dextrin; pectin; chitin; chitosan; pullulan; gluten; levan; sodium alginate; agar; algin; carrageenan; gellan; furcellaran; elsinan; protein-based polymers, such as collagen; soy protein isolate; whey protein isolate; casein; polyhydroxy acid polymers; polyquaternium polymers; polyacrylic acid polymers; methylmethacylate copolymers, carboxyvinyl polymers; poly(2-ethyl-2-oxazoline (sold as AQUAZOL 500 by Ashland, Inc.); or combinations thereof.

HPMC, mentioned above, is a water-soluble, non-ionic cellulose ether. HPMC also can function as a thickener, a lather enhancer, a lather stabilizer, a foam stabilizer, a water-binder, a co-suspending agent, or a co-emulsifying agent. When HPMC is incorporated into the sheet soap and the sheet soap is mixed with water to form a foam, the properties of HPMC maintain water inside the foam for enhanced cleaning capability. When the foam is dispensed onto the surface of a tissue, the water maintained inside the foam delays water penetration through a tissue, maintaining the tissue integrity during cleaning.

The addition of one or more ionic cross-linkers affords the sheet soap a bending resistance in a range between about 1 mgf and about 50 mgf. Bending resistance of the sheet soap is measured by TAPPI test method T 543 om-11, which is incorporated herein in its entirety by reference. In one aspect, the sheet soap's bending resistance is in a range between about 1 mgf and about 100 mgf. In another aspect, the sheet soap has a bending resistance in a range between about 1 mgf and about 20 mgf. For comparison, Post-It® paper has a bending resistance of about 84.91 mgf. Plastic sheets have a bending resistance of about 28.58 mgf. Hand towels have a bending resistance of about 10.28 mgf in the machine direction, and tissue base-sheets have a bending resistance of less than about 0.2 mgf. Thus, sheet soaps in accordance with the present invention have a desirable bending resistance, being not overly flexible or overly brittle. The bending resistance of the inventive sheet soaps plays an important role in improving the sheet soap production process. Further, the bending resistance of the inventive sheet soaps enables the sheet soaps to be dispensed from a manual or an electronic dispenser.

The sheet soap can include one or more fillers substantially uniformly dispersed within contact product of the sheet soap. A filler is any chemically inert organic or inorganic material which can be added to the sheet soap to alter a desired property, such as the consistency. For example, fillers can dilute the active ingredients, increase solubility, modify texture, or impart a color to the sheet soap. Fillers are generally dry powders. Thus, the sheet soap properties can be tailored to provide any desired texture or aesthetic.

In one aspect, the sheet soap includes an emollient. In another aspect, the emollient is disposed onto one or more sides as a layer. Yet, in another aspect, the emollient is substantially uniformly dispersed within the contact product of the sheet soap. Emollients hydrate the skin by reducing evaporation from the surface. When the emollient layer is disposed on the outer surface of the soap, the soap's integrity is protected from the environment. For example, a high humidity or dry environment can alter the physical properties of the sheet soap, inducing brittleness, dryness, or increased tackiness.

In another aspect, the sheet soap can include at least one additive substantially uniformly dispersed within the contact product of the sheet soap. Additives can be selected to provide any desired skin care benefit. Yet, in another aspect, the at least one additive is an essential oil, a humectant, an antioxidant, a buffer, a fragrance, a colorant, or any combination thereof.

The sheet soap of the present invention can be in any convenient shape or size. The user can removably dispose the desired amount of sheet soap within the dispenser as desired. In one aspect, the sheet soap is a continuous sheet, which is cut into individual pieces by the user as needed. The sheet can be in the form of a roll. In another aspect, the sheet soap roll includes perforations or indentions to indicate a pre-determined amount of soap for a given application. In another aspect, the sheet soap is manufactured as individual sheets. Yet, in another aspect, the sheet soap is a cube shape. Still yet, in another aspect, the sheet soap is rectangular prism shape. In another aspect, the sheet soap is a cylinder shape.

Sheet soap thickness can be tailored as desired. The thickness is determined by the liquid coating thickness during production, which is discussed below. In one aspect, the sheet soap thickness is in the range between about 25 microns and about 275 microns. In another aspect, the thickness is in the range between about 50 microns and about 250 microns. Yet, in another aspect, the thickness is in the range between about 75 microns and about 225 microns. Still yet, in another aspect, the thickness is in the range between about 100 microns and about 200 microns.

Ionic Cross-Linker Composition

As discussed above, the film-forming composition comprises an ionic cross-linker composition. The ionic cross-linker is present a range between about 1% and about 10% by weight of the total weight of the sheet soap. In one aspect, the ionic cross-linker is in a range between about 2% and about 8% by weight of the total weight of the sheet soap. In another aspect, the ionic cross-linker is present in a range between about 1% and about 4% by weight of the total weight of the sheet soap. Yet, in another aspect, the ionic cross-linker is present in a range between about 3% and about 6% by weight of the total weight of the sheet soap. Still yet, in another aspect, the ionic cross-linker is about or in any range between about 1%, 2%, 3%, 4%, 5%, 6%, 7%, 8%, 9%, and 10% by weight of the total weight of the sheet soap.

Examples of ionic cross-linkers include, but are not limited to, polyvalent amines such as diamines, triamines, polyamines, or salts of these amines; polyvalent metal hydroxides such as aluminum hydroxide, calcium hydroxide, magnesium hydroxide, or zinc hydroxide; polyvalent metal oxides such as aluminum oxide, calcium oxide, zirconium oxide, magnesium oxide, lead oxide, or zinc oxide; polyvalent metal inorganic salts such as aluminum sulfate, aluminum potassium sulfate, aluminum carbonate, aluminum chloride, calcium sulfate, calcium carbonate, calcium chloride, magnesium sulfate, magnesium carbonate, magnesium chloride, zinc sulfate, zinc carbonate, zinc gluconate, zinc lactate, zinc chloride, or aluminum methasilicate; polyvalent metal organic salts such as aluminum acetate, calcium acetate, magnesium acetate, zinc acetate, aluminum glycinate, ammonium zirconium carbonate, potassium zirconium carbonate, zirconium acetate, zirconium stearate; alkali earth metal salts of thioglycolic acid, such as calcium or magnesium; or combinations thereof.

Surfactant Composition

The sheet soap includes one or more surfactants, including cationic surfactants, anionic surfactants, nonionic surfactants, amphoteric surfactants, and combinations thereof. One or more types of surfactants or various mixtures of the foregoing surfactants can be used to modify the desired properties of the composition. The surfactant composition is present in a range between about 40% and about 60% by weight of the total weight of the sheet soap. In one aspect, the surfactant composition is present in a range between about 40% and about 50% by weight of the total weight of the sheet soap. In another aspect, the surfactant composition is present in a range between about 45% and about 55% by weight of the total weight of the sheet soap. Yet, in another aspect, the surfactant composition is present in a range between about 50% and about 60% by weight of the total weight of the sheet soap. Still yet, in another aspect, the surfactant composition is about or in any range between about 40%, 42%, 45%, 47%, 50%, 52%, 55%, 57%, and 60% by weight of the total weight of the sheet soap.

Examples of cationic surfactants include, but are not limited to, long chain amines; quaternary ammonium salts such as di($C_8$-$C_{24}$)alkyldimethylammonium chloride or bromide; di($C_{12}$-$C_{18}$)alkyldimethylammonium chloride or bromide; distearyldimethylammonium chloride or bromide; ditallowalkyldimethylammonium chloride or bromide; dioleyldimethylammonium chloride or bromide; dicocoalkyldimethylammonium chloride or bromide; ($C_8$-$C_{24}$) alkyldimethylethylammonium chloride or bromide; ($C_8$-$C_{24}$) alkyltrimethylammonium chloride or bromide; cetyltrimethylammonium chloride or bromide; ($C_{20}$-$C_{22}$) alkyltrimethylammonium chloride or bromide; ($C_8$-$C_{24}$) alkyldimethylbenzyl-ammonium chloride or bromide; N—($C_{10}$-$C_{18}$)alkylpyridinium chloride or bromide; N—($C_{10}$-$C_{18}$)alkylisoquinolinium chloride, bromide or monoalkylsulfate; N—($C_{12}$-$C_{18}$)alkylpolyoylaminoformylmethylpyridinium chloride; N—($C_{12}$-$C_{18}$)alkyl-N-methylmorpholinium chloride, bromide or monoalkylsulfate; N—($C_{12}$-$C_{18}$)alkyl-N-ethylmorpholinium chloride, bromide or monoalkylsulfate; ($C_{16}$-$C_{18}$)alkylpentaoxethylammonium chloride; diisobutylphenoxyethoxyethyldimethylbenzylammonium chloride; salts of N,N-diethylaminoethylstearylamide and -oleylamide with hydrochloric acid, acetic acid, lactic acid, citric acid, and phosphoric acid; N-acylaminoethyl-N,N-diethyl-N-methylammonium chloride, bromide or monoalkylsulfate; and N-acylaminoethyl-N,N-diethyl-N-benzylammonium chloride, bromide or monoalkylsulfate, where acyl is stearyl or oleyl; and combinations thereof.

Examples of anionic surfactants include, but are not limited to, sulfates, such as sodium laureth sulfate; ammonium laureth sulfate; alkylpolysaccharide sulfates, such alkylpolyglycoside sulfates; branched primary alkyl sulfates; alkyl glyceryl sulfates; alkenyl glyceryl sulfates; alkylphenol ether sulfates; or oleyl glyceryl sulfates; alkyl succinates; sulfonates, such as alkylbenzene sulfonates; or alkyl ester sulfonates, including linear esters of $C_8$-$C_{20}$-carboxylic acids (i.e., fatty acids) which are sulfonated by means of gaseous $SO_3$ carboxylates; phosphates, such as alkyl phosphates; alkyl ether phosphates; isethionates, such as acyl isethionates; sulfosuccinates, including monoesters of sulfosuccinates (such as saturated and unsaturated $C_{12}$-$C_{18}$ monoesters); or diesters of sulfosuccinates (such as saturated and unsaturated $C_{12}$-$C_{18}$ diesters); acyl sarcosinates, such as those formed by reacting fatty acid chlorides with sodium sarcosinate in an alkaline medium; salts of acylaminocarboxylic acids, such as salts of alkylsulfamidocarboxylic acids; N-acyltaurides; and combinations thereof. Suitable starting materials for anionic surfactants are natural fats, such as tallow, coconut oil and palm oil, but can also be of a synthetic nature.

Examples of nonionic surfactants include, but are not limited to, glucosides, such as lauryl glucoside and decyl glucoside, and the ethoxylated alcohols and ethoxylates of long-chain, aliphatic, synthetic or native alcohols having a $C_8$-$C_{22}$ alkyl radical. These ethoxylated alcohols and can contain from about 1 to about 25 moles of ethylene oxide. The alkyl chain of the aliphatic alcohols can be linear or branched, primary or secondary, saturated or unsaturated. Condensation products of $C_{10}$-$C_{18}$ alcohols with from about 2 to about 18 moles of ethylene oxide per mole of alcohol can be used. The alcohol ethoxylates can have a narrow homolog distribution ("narrow range ethoxylates") or a broad homolog distribution of the ethylene oxide ("broad range ethoxylates"). Amides-fatty acid combinations, such as coconut amides, including cocamide diethanolamine, cocamide monoethanolamine, are also useful.

Examples of amphoteric surfactants include, but are not limited to, betaines, sultaines, imidazoline derivatives, and the like. Typical amphoteric surfactants include disodium cocoamphodiacetate, ricinoleamidopropyl betaine, cocamidopropyl betaine, stearyl betaine, stearyl amphocarboxy glycinate, sodium lauraminopropionate, cocoamidopropyl hydroxy sultaine, disodium lauryliminodipropionate, tallow-iminodipropionate, cocoampho-carboxy glycinate, cocoimidazoline carboxylate, lauric imidazoline monocarboxylate, lauric imidazoline dicarboxylate, lauric myristic betaine, co coamidosulfobetaine, alkylamidophospho betaine, and combinations thereof.

In addition to the foregoing surfactants, suitable blends of surfactants include, but not limited to, blends of liner alkylbenzene sulfonate, coconut amide, and mixed ethoxylated alcohols (sold as COLADET SDC by Colonial Chemical, Inc., South Pittsburgh, Tenn.); blends of anionic-amide surfactants (sold as COLADET DC-6 by Colonial Chemical, Inc.); blends of ammonium laureth sulfate, disodium cocoamphodiacetate, lauryl glucoside, decyl glucoside, and cocamidopropyl betaine (sold as COLADET GBP by Colonial Chemical, Inc.); blends of potassium cocoate (sold as COLADET KC-40 by Colonial Chemical, Inc.); proprietary blends of nonionic surfactants, for example COLADET RA-300 by Colonial Chemical, Inc.; or any combination thereof.

The sheet soap can include a foam booster agent. Examples of suitable foam booster agents include, but are not limited to, alkyldimethylamine oxide, caprylyl pyrrolidone, cocamide MEA, cocamide DEA, cocamidopropyl betaine, cocamidopropyl dimethyamine lactate, cocamidopropyl hydroxysultaine, coco-betaine, cocamidopropyl betaineamide MEA chloride, cocamidopropyl dimethyamino hydroxypropyl hydrolyzed collagen, cocamidopropyl oxide lauramine oxide, lauramide DEA, myristamine oxide, oleyl betaine, dimethyl lauramide, sodium cocoamphoacetate, sodium cocoylisethionate, sodium laureth sulfate, soyamidpropyl betaine, or any combination thereof.

Optionally, the sheet soap includes a hydrotrope, which is a compound that enhances water-solubility of hydrophobic compounds in aqueous solutions. Non-limiting examples of hydrotropes include ammonium cumene sulfonate, ammonium xylenesulfonate, cetamine oxide, cocamidopropylamine oxide, lauramine oxide, potassium toluenesulfonate, PPG-2-isodeceth-4-6-9-12, sodium cumene sulfonate, sodium laureth-13-carboxylate, sodium toluene sulfonate, sodium xylene sulfonate, taidecceth-19-carboxylic acid, or any combination thereof.

The sheet soap can include a foam stabilizer. Non-limiting examples of foam stabilizers include behenamine oxide, caprylyl pyrrolidone, dihydroxyethyl cocamine oxide, erucamidopropyl hydroxyl sultaine, hydroxypropyl methycellulose, lauryl pyrrolidone, palmitamide MEA, ricinoleamide MEA, sesamide DEA, wheat germamide DEA, pectin, PEG-3 lauramide, PEG-4 oleamide, PEG-5 cocamide, PEG-6 lauramide, or any combination thereof.

Antimicrobial Composition

The sheet soap can include an antimicrobial composition in a range between about 1% and about 5% by weight of the total weight of the sheet soap. In one aspect, the antimicrobial composition is present in a range between about 2% and about 4% by weight of the total weight of the sheet soap. In another aspect, the antimicrobial composition is present in a range between about 1% and about 3% by weight of the total weight of the sheet soap. Yet, in another aspect, the antimicrobial composition is present in a range between about 3% and about 5% by weight of the total weight of the sheet soap. Still yet, in another aspect, the antimicrobial composition is present about or in any range between about 0.5%, 1%, 1.5%, 2%, 2.5%, 3%, 3.5%, 4%, 4.5% and 5% by weight of the total weight of the sheet soap.

Antimicrobial agents can be natural, such as antimicrobial agents of vegetal or animal origin, synthetic, or combinations thereof. Examples of anti-microbial agents include, but are not limited to, bioflavonoids such as hesperitin, naringin, catechin, L-canavanine, quercetin, epigallocatechin gallate, robinetin, myricetin, apigenin, rutin, galanin, or lonchocarpol A; fatty acids such as caprylic acid, or perlargonic acid; quinolones such as hydroxyquinoline sulfate, 8-hydroxyquinoline, 8-hydroxyquinoline citrate, or oxyquinoline; silver salts such as silver sulphadiazine; chlorhexidine salts such as gluconate, chlorhexidene digluconate, chlorhexidene acetate, chlorhexidene isethionate, or chlorhexidene hydrochloride; quaternary ammonium salts; EDTA salts such as tetrasodium EDTA; dicarboxylic acids such as malonic, glutaric, citric, succinic, or diglycolic acids; alpha hydroxy carboxylic acids, such as D-galacturonic acid; zinc salts; neem seed oil; sandalwood oil; or any combination thereof.

Emollients

The sheet soap can include an emollient composition. The emollient composition can be incorporated as a layer disposed onto one or more sides of the sheet soap. In one aspect, the emollient layer is disposed onto one side of the sheet soap. In another aspect, the emollient layer is disposed onto all sides of the sheet soap. Yet, in another aspect, one or more emollients are substantially uniformly dispersed within the sheet soap contact product.

The emollient composition can include one or more polar emollients and/or nonpolar emollients in a range between about 1% and about 5% by weight of the total weight of the sheet soap. In one aspect, the emollient composition is present in a range between about 2% and about 4% by weight of the total weight of the sheet soap. In another aspect, the emollient composition is present in a range between about 1% and about 3% by weight of the total weight of the sheet soap. Yet, in another aspect, the emollient composition is present in a range between about 3% to about 5% by weight of the total weight of the sheet soap. Still yet, in another aspect, the emollient composition is present about or in any range between about 0.5%, 1%, 1.5%, 2%, 2.5%, 3%, 3.5%, 4%, 4.5%, and 5% by weight of the total weight of the sheet soap.

Examples of polar emollients include, but are not limited to, alcohols, such as propylene glycol, glycerol, diethylene glycol, methylene glycol, polypropylene glycol, polyethylene glycol, sorbitol, and mixtures thereof. Suitable nonpolar emollients include, but are not limited to, aromatic or linear esters, such as Guerbet ester, mineral oil, squalane, liquid paraffin, isopropyl myristate, tri-octyldodecyl-citrate, carnation oil, silicone oil, dimethicone siloxane, cyclo-dimethicone siloxane, and mixtures thereof.

Fillers

The sheet soap can include one or more fillers in a range between about 0% to about 2% by weight of the total weight of the sheet soap. In one aspect, the filler is present in a range between about 0.5% and about 2.5% by weight of the total weight of the sheet soap. In another aspect, the filler is present in a range between about 1% and about 2% by weight of the total weight of the sheet soap. Yet, in another aspect, the filler is present in a range between about 0.5% and about 1.5% by weight of the total weight of the sheet soap.

Examples of fillers include, but are not limited to, silica, such as treated silica, silicates, such as chemically modified magnesium aluminum silicate, hydrated aluminum silicate, aluminum starch octenyl succinate barium silicate, calcium silicate, magnesium silicate, or strontium silicate, stearates, such as zinc stearate, magnesium stearate, or aluminum stearate, zinc myristate, calcium palmitate, talc, mica, kaolin, organasol, polyethylene powder, polytetrafluoroethylene (sold as TEFLON by DuPont, Wilmington, Del.), starch, boron nitride, copolymer microspheres (sold as EXPANCEL by AkzoNobel, Duluth, Ga.), silicone resin microbeads, chalk, Fuller's earth, kaolin, sericite, muscovite, lepidolite, biotite, vermiculite, alkyl and/or trialkyl aryl ammonium smectites, organically modified montmorillonite clay, zeolite, barium sulfate, calcined calcium sulfate (calcined gypsum), hydroxyapatite, ceramic powder, colloidal silicon dioxide, boron nitride, polyamide resin powder (nylon powder), cyclodextrin, methyl polymethacrylate powder, benzoguanamine resin powder, poly(ethylene tetrafluoride) powder, carboxyvinyl polymer, cellulose powder, ethylene glycol monostearate, and combinations thereof.

Additives

The sheet soap can include additives known in the art. Optional skincare benefit additives include any additive known in the art for skin healing, skin soothing, skin pH balance, skin pain relief, skin cooling effects, skin warming effects, skin freshness, and skin disinfecting. All of these optional materials are well known in the art.

When an additive is employed, it is present in a range between about 1% to about 2% by weight of the total weight of the sheet soap. In another aspect, an additive is present in a range between about 0.5% and about 2.5% by weight of the total weight of the sheet soap. Yet, in another aspect, an additive is present in a range between about 0.5% and about 1.5% by weight of the total weight of the sheet soap.

Exemplary additives used for skin healing include, but are not limited to, vitamin E, allantoin, candelilla wax, aloe vera, tamanu oil, petrolatum, calamine, dimethicone, cocoa butter, shark liver oil, glycerin, zinc oxide, aluminum hydroxide, kaolin, zinc acetate, zinc carbonate, and combinations thereof. Optional skin soothing additives include, but are not limited to, natural moisturizing and soothing botanical extracts, anti-inflammatory agents, and combinations thereof. Exemplary moisturizing additives include, but are not limited to, esters, humectants, natural botanical extracts, such as chamomile *recutita* extract, *sambucus nigra* extract, *primula veris* extract, glycerin, *helianthus annuus* extract, phospholipids, silicones, occlusive agents, natural oils, barbadensis gel, and combinations thereof.

Optional skin pain relief/numbing additives include, but are not limited to, benzocaine, lidocaine, tetracaine, capsaicin, ketoprofen, diclofenac, ibuprofen, ketamine, dibucaine, butamben picrate, pramoxine, and combinations thereof. Exemplary additives for skin cooling effects include, but are not limited to, menthol, isopulegol, menthol derivatives, such as menthyl lactate, menthol propylene glycol carbonate, menthol ethylene glycol carbonate, menthyl pyrrolidone carboxylic acid, menthyl methyl ether, menthoxypropane diol, menthone glycerine acetal, monomenthyl succinate, menthyl glycolate, 2-hydroxymethyl-3,5,5-trimethylcyclohexanol, and combinations thereof.

Exemplary additives for skin warming effects include, but are not limited to, ginger oil, polyhydric alcohols, *capsicum* (red pepper) powder, a *capsicum* tincture, *capsicum* extract, capsaicin, homocapsaicin, homodihydrocapsaicin, nonanoyl vanillyl amide, nonanoic acid vanillyl ether, vanillyl alcohol alkyl ether derivatives, such as vanillyl ethyl ether, vanillyl butyl comprising ether, vanillyl pentyl ether, vanillyl hexyl ether, isovanillyl alcohol alkyl ether, or ethylvanillyl alcohol alkyl ether, veratryl alcohol derivatives, substituted benzyl alcohol derivatives, vanillin propylene glycol acetal, ethylvanillin propylene glycol, ginger extract, gingeol, gingeron, and combinations thereof.

Essential oils are any volatile oils obtained from plants that possess the odor and other characteristics properties of the plant. Essential oils useful in the present invention include, but are not limited to, basil, bergamot, blue cypress, cajeput, cardamom, carrot seed, *cassia*, catnip, chamomile, clary sage, clove bud, cedarwood, cinnamon, coffee, cognac (green), coriander, cumin, cypress, *eucalyptus* (lemon), *eucalyptus*, fennel, foraha, frankincense, geranium, german chamomile, grapefruit, helichrysum, hyssop, jasmine, juniperberry, lavender, lemon, lemongrass, lime, *litsea cubeba*, mandarin, myrrh, neem seed, neroli, orange, patchouli, pepper (black), peppermint, roman chamomile, rose, rosehip, rosemary, rosewood, sandalwood, spearmint, spruce, St. John's wort, tangerine, tea tree, thyme, valerian, vetiver, violet, ylang ylang, and combinations thereof.

Humectants are hygroscopic materials with a two-fold moisturizing action including water retention and water absorption. Humectants prevent the loss of moisture from skin and help to attract moisture from the environment. Suitable humectants include, but are not limited to, glycerol, hydrolyzed silk, ammonium lactate, hydroxypropyltrimonium hydrolyzed silk, hydroxypropyl chitosan, hydroxypropyltrimonium hydrolyzed wheat protein, lactamidopropyltrimonium chloride, ethyl esters of hydrolyzed silk, and combinations thereof.

Illustrative antioxidants for use in the present invention include, but are not limited to, alpha tocopherol, ascorbic acid, acorbyl palmitate, butylated hydroxyanisole, butylated hydroxytoluene, potassium metabisulfite, propionic acid, propyl gallate, sodium ascorbate, sodium bisulfite, sodium metabisulfite, sodium sulfite, and combinations thereof.

Suitable buffers include agents that reduce pH changes. Illustrative of buffering agents include carbonates, phosphates, bicarbonates, citrates, borates, acetates, phthalates, tartrates, and succinates. Non-limiting examples of suitable buffering agents include aluminum-magnesium hydroxide, aluminum glycinate, calcium acetate, calcium bicarbonate, calcium borate, calcium carbonate, calcium citrate, calcium gluconate, calcium glycerophosphate, calcium hydroxide, calcium lactate, calcium phthalate, calcium phosphate, calcium succinate, calcium tartrate, dibasic sodium phosphate, dipotassium hydrogen phosphate, dipotassium phosphate, disodium hydrogen phosphate, disodium succinate, dry aluminum hydroxide gel, magnesium acetate, magnesium aluminate, magnesium borate, magnesium bicarbonate, magnesium carbonate, magnesium citrate, magnesium gluconate, magnesium hydroxide, magnesium lactate, magnesium metasilicate aluminate, magnesium oxide, magnesium phthalate, magnesium phosphate, magnesium silicate, magnesium succinate, magnesium tartrate, potassium acetate, potassium carbonate, potassium bicarbonate, potassium borate, potassium citrate, potassium metaphosphate, potassium phthalate, potassium phosphate, potassium polyphosphate, potassium pyrophosphate, potassium succinate, potassium tartrate, sodium acetate, sodium bicarbonate, sodium borate, sodium carbonate, sodium citrate, sodium gluconate, sodium hydrogen phosphate, sodium hydroxide, sodium lactate, sodium phthalate, sodium phosphate, sodium polyphosphate, sodium pyrophosphate, sodium sesquicarbonate, sodium succinate, sodium tartrate, sodium tripolyphosphate, synthetic hydrotalcite, tetrapotassium pyrophosphate, tetrasodium pyrophosphate, tripotassium phosphate, trisodium phosphate, trometarnol, and combinations thereof.

The sheet soap can optionally include fragrances and encapsulated fragrances. Suitable fragrances include, but are not limited to, volatile aromatic esters, non-aromatic esters, aromatic aldehydes, non-aromatic aldehydes, aromatic alcohols, non-aromatic alcohols, heterocyclic aroma chemicals, natural floral fragrances such as blossom, carnation, *gardenia*, geranium, iris, hawthorne, hyacinth and jasmine, and combinations thereof.

Examples of colorants or pigments include, but are not limited to, any additive used as a colorant in foods, such as red food dye, orange food dye, yellow food dye, green food dye, blue food dye, or violet food dye, metal oxide pigments, such as titanium dioxide, zirconium oxide, cerium oxide, zinc oxide, iron oxide (black, yellow or red), or chromium oxide, manganese violet, ultramarine blue, carbon black, cochineal carmine, copper sulfate, iron sulfate, water-soluble sulfopolyesters, rhodamines, natural dyes, such as carotene, beetroot juice, methylene blue, caramel, and combinations thereof.

Method of Making the Sheet Soap

The sheet soap 30 of the present invention includes an ionic cross-linker that assists in providing a sheet soap that is strong enough, yet flexible, and not overly brittle. The cross-linker improves the sheet soap's physical properties to satisfy production requirements and enables, along with the polyvinyl alcohol and film-forming material, the soap to be dispensed from any dispenser or from a sheet soap roll. In addition, perforations or indentions can be incorporated into the sheet soap roll. These perforations or indentions promote use of effective amounts of sheet soap because the user can easily tear an appropriate sized piece to use in the dispenser. Thus, the user can easily replace the sheet soap 30 in the dispenser 40 to prepare a fresh foamable solution 34.

The sheet soap 30 made in accordance with the present invention can be formed by techniques known in the industry. For example, the film-forming polymer composition is combined with other components, including one or more ionic cross-linkers, fillers, surfactants, antimicrobial agents, and/or additives, in water or solvent. The composition is dispersed onto a surface and dried into sheet/film form. Sheet soaps are formed from such dispersions or solutions by shaping them into a solidified form of suitable thickness by techniques known in the art (e.g., wet casting, freeze-drying, and extrusion molding). The dispersion or solution can be directly coated or sprayed onto another product and dried to form a sheet or film.

Sheet soaps can be prepared by applying a solution or dispersion of the components to a substrate to form a coating. The sheet soap coating formulation is prepared by making a solution or dispersion of the desired components, applying the mixture to a substrate, using knife, bar, or extrusion die coating methods, drying the coated substrate to remove at least part of the solvent, and removing the resulting soap sheet/film from the substrate. Examples of substrates include silicone elastomers, metal foils and metalized polyfoils, composite foils or films containing polytetrafluoroethylene materials or equivalents thereof, polyether block amide copolymers, polyurethane, polyvinylidene, polyester, and other such materials useful in the art as releasable substrates. The sheet soap is dried at standard temperature and/or pressure, or at lower or elevated temperature and/or pressure compared to standard conditions.

A coating of any desired additive or component can be applied to the soap sheet/film following formation. The coating can include, for example, humectants or moisturizers. In one aspect, the coating includes one or more emollients. The emollient coating provides a skin moisturizing benefit. In addition, the emollient coating provides a moisture barrier to protect the integrity of the sheet soap from the environment. A high humidity environment or dry environment can alter the physical properties of the sheet soap and induce brittleness, breaking, drying, or increased tackiness.

Any additive coating can be applied by any suitable methods known to those in the art. The coating can be applied to one or both sides of the sheet soap. In one aspect, the coating is sprayed onto one or both sides of the sheet soap. Other exemplary methods to apply a coating include, but are not limited to, dipping the soap in the coating, or brushing the coating on the soap.

Solid particles can also be incorporated in the films. Solid particles include, for example, exfoliating beads, encapsulated ingredients, or decorative elements. Encapsulated ingredients include fragrances, anti-microbial agents, color-changing indicators, i.e. color-changing indicators activated by pH changes.

The sheet soaps can be partially dried, in that some degree of water or other solvent remains. The amount of solvent present in the sheet soap can be controlled to obtain desired functionality. For example, more water/solvent can result in a more flexible sheet, while too much solvent can result in a sheet soap that is tacky. Some solvent can generally remain in the personal cleansing film as used.

The sheet soaps made in accordance with the present invention exhibit moisture and blocking resistance, yet are wetted when exposed to water or a polar solvent followed by rapid dissolution. The speed at which the sheet soaps wet and dissolve can be modified by one skilled in the art to target a specific delivery profile. For example, more rapid dissolution of carboxylated water soluble polymers can be achieved using neutralization. Neutralizing carboxylic groups of water soluble polymers creates charged carboxyl groups along the polymer. The charged polar groups make these sections of the polymer more soluble in polar solvents than if these carboxyl groups were not neutralized.

Method of Making the Foam Soap Delivery System

Although the method of making the sheet soap 30 is described above, it is to be noted that the paperboard core 20, plurality of sheets of paper or tissue 26 wound around the paperboard core 20, and the dispenser 40 can be manufactured by any methods known in the art. The initial step of assembly is removably disposing the sheet soap 30 within the dispenser 40. One or more sheet soaps can be packaged within the dispenser 40. The next step includes sealing the sheet soap 30 within the dispenser 40, which can include removably and sealably engaging the container 60 of the dispenser 40 with a pump 42 or cap 80. The final step of assembly is removably disposing the dispenser 40 within the paperboard core 20. Optionally, a hanger 70 can be removably or permanently disposed on the dispenser 40.

Use

The foam soap delivery system 10 is convenient for general travel or transportation because it is lightweight, lacking additional weight from water or liquids. In addition, the system is convenient for airplane travel, which restricts liquid volumes in carry-on baggage. Further, the packaged system is waterless, reducing the risk of leakage compared to conventional liquid or foam soaps.

When ready to use the system 10, the user removes the dispenser 40 from the paperboard core 20 and tears one or more sheets of the paper or tissue from the plurality of sheets 26. Next, the user opens the dispenser 40 by removing the pump 42 or cap 80 and adds water 32 to the dispenser 40 comprising the sheet soap 30. The user replaces the pump 42 or cap 80 to seal the dispenser 40 and shakes to dissolve the sheet soap 30, forming a substantially uniform foamable solution 34. Shaking or agitating the foamable solution 34 induces production of a foam 36 within the dispenser 40. Finally, the user discharges the foam 36 onto the one or more sheets of paper or tissue 28. Alternatively, the user discharges the foam 36 directly onto skin or hair.

As described above, a hand-actuatable pump 42 can mix air with the foamable solution 34 to produce foam 36 upon actuation by the user. In another aspect, a motion-actuated pump 42 having a sensor 44 that senses motion of the user can mix air with the foamable solution 34 to produce and discharge foam 36 upon sensing motion. Yet, in another aspect, the user can shake, agitate, rock, or swirl the foamable solution 34 to produce sufficient foam 36, which can be dispensed by any dispenser 40. In addition to water, a user can add any other solution with one or more additives to the dispenser 40 comprising the sheet soap 30. Any additional surfactants, antimicrobials, emollients, or additives described above for the sheet soap are suitable.

The dispenser 40 can be re-used or emptied as desired. The ability to re-use the dispenser 40, requiring the user to purchase only additional sheet soaps 30, reduces expense and waste.

In addition, the present invention provides a system 10 for dispensing a metered amount of foam 36. The dispenser 40 discharges the metered amount of foam 36 upon stimulation by a user when sufficient water 32 is present within the dispenser 40 to produce an effective concentration of the foamable solution 34. Effective concentration of the sheet soap 30 depends on the ratio of sheet soap 30, measured in milligrams (mg) to volume of water 32, measured in milliliters (mL). The effective concentration of the foamable solution 34 is defined as at least 1 milligram of sheet soap 30 per milliliter of water 32. In one aspect, the effective concentration of the sheet soap 30 is in a range between about 1 mg/mL and about 100 mg/mL. In another aspect, the effective concentration of the sheet soap is in a range between about 1 mg/mL and about 15 mg/mL.

Yet in another aspect, the sheet soap forms a foam soap liquid when the sheet soap concentration is between about 1 mg/mL and about 50 mg/mL. The foam soap liquid has a viscosity in a range between about 1 centipoise (cp) and about 100 cp. In another aspect, the resulting foam soap liquid has a viscosity in a range between about 1 cp and about 50 cp. Viscosity is measured at room temperature. For example, viscosity can be measured in a 300 mL beaker with a viscometer, such as a Brookfield digital viscometer Model DV-E, with spindle #61, and a rotational speed 10 RPM (Brookfield Engineering Laboratories, Inc., Middleboro, Mass.).

Still yet, in another aspect, the sheet soap forms a gel-like foam when the concentration is between about 50 mg/mL and about 100 mg/mL. The gel-like foam has a viscosity greater than about 100 cp. In another aspect, the viscosity is greater than about 50 cp.

The system 10 can be packaged with a sheet soap 30 of sufficient size to form a foamable solution 42 with an effective concentration. Additional sheet soap 30 can be packaged with the system as a roll of sheet soap. Perforations present in the sheet soap roll, as described above, can designate the appropriate amount of sheet soap 30 required to form an effective concentration within the dispenser 40.

To provide a more complete understanding of the present invention and not by way of limitation, reference is made to the following examples. Accordingly, the examples are to be regarded in an illustrative rather than restrictive sense, and all such modifications are intended to be included within the scope of the present invention.

EXAMPLES

In examples 1-23, all ingredients were blended at room temperature until uniform in solution. The solution then was cast onto a 70 millimeter diameter aluminum dish with an appropriate weight. Then, about 1.25-1.75 grams of soap solution was dried in an oven at 105° C. to achieve a film soap weight of about 0.5 to 0.7 grams.

Comparative Examples 1-7

In comparative Examples 1-5, sheet soaps were prepared without a cross-linker. In Examples 6-7, sheet soaps were prepared with cross-linkers in accordance with the present invention (Table 1). Masses of all components were measured in grams (g).

TABLE 1

| | Example | | | | | | |
|---|---|---|---|---|---|---|---|
| | 1 | 2 | 3 | 4 | 5 | 6 | 7 |
| COLADET SDC[1] | 3 g | 3 g | 3 g | 3 g | 3 g | 3 g | 3 g |
| KLUCEL[2] | — | — | — | — | — | 0.5 g | 0.5 g |
| AQUAZOL 500[3] | 0.5 g | — | — | — | — | — | — |
| Carboxymethyl cellulose | — | 0.5 g | — | — | — | — | — |
| DISINTEX 600[4] | — | — | 0.5 g | — | — | — | — |
| DISINTEX 75[5] | — | — | — | 0.5 g | — | — | — |
| KURARAY KL-506[6] | 1.5 g | 1.5 g | 1.5 g | 1.5 g | 1.5 g | 1.5 g | 1.5 g |
| VIVIPRINT PS-10[7] | — | — | — | — | 0.5 g | — | — |
| Zinc carbonate | — | — | — | — | — | — | 0.05 g |
| Zinc lactate | — | — | — | — | — | 0.05 g | — |
| Blue dye | — | — | — | — | — | — | 0.001 g |
| Green dye | — | — | — | — | — | 0.001 g | — |

[1]COLADET SDC: alkylbenzene sulfonate, coconut amide, and mixed ethoxylated alcohols
[2]KLUCELL: hydroxypropyl cellulose
[3]AQUAZOL 500: poly(2-ethyl-2-oxazoline)
[4]DISINTEX 600: urea, 2-pyrrolidinone-1-ethenyl-homopolymer, cellulose
[5]DISINTEX 75: polyvinyl pyrrolidone
[6]KURARAY KL-506: polyvinyl alcohol
[7]VIVIPRINT PS-10: 2-pyrrolidinone-1-ethenyl homopolymer Examples 8-10

In Examples 8-11, sheet soaps were prepared in accordance with the present invention (Table 2). Masses of all components were measured in grams (g). Percent weights "%" indicate percent by weight of the total weight of the sheet soap, including all components.

TABLE 2

|  | Example | | |
|---|---|---|---|
|  | 8 | 9 | 10 |
| COLADET SDC[1] | 57% | 56% | 55% |
| Carboxymethyl cellulose | 10% | 10% | 10% |
| KURARY KL-506 (15%)[2] | 30% | 30% | 30% |
| Zinc carbonate | 1% | 2% | 2% |
| Caprylic acid | 1% | 1% | 1% |
| Nonanoic acid | 1% | 1% | 1% |
| Zinc gluconate | — | — | 1% |

[1]COLADET SDC alkylbenzene sulfonate, coconut amide, and mixed ethoxylated alcohols
[2]KURARY KL-506 polyvinyl alcohol

Examples 11-20

In Examples 11-20, sheet soaps were prepared in accordance with the present invention (Table 3). Masses of all components were measured in grams (g). Percent weights "%" indicate percent by weight of the total weight of the sheet soap, including all components.

TABLE 3

|  | Example | | | | | | | | | |
|---|---|---|---|---|---|---|---|---|---|---|
|  | 11 | 12 | 13 | 14 | 15 | 16 | 17 | 18 | 19 | 20 |
| COLADET SDC[1] | 55% | — | — | — | — | 55% | — | — | — | — |
| COLADET DC-6[2] | — | 55% | — | — | — | — | 55% | — | — | — |
| COLADET RA[3] | — | — | 55% | — | — | — | — | 55% | — | — |
| COLADET GBP[4] (50%) | — | — | — | 55% | — | — | — | — | 55% | — |
| COLADET KC-40[5] (40%) | — | — | — | — | 55% | — | — | — | — | 55% |
| Carboxymethyl cellulose | — | — | — | — | — | 2% | 2% | 2% | 2% | 2% |
| KLUCELL[6] | 10% | 10% | 10% | 10% | 10% | 8% | 8% | 8% | 8% | 8% |
| KURARAY KL-506[7] (50%) | 30% | 30% | 30% | 30% | 30% | 30% | 30% | 30% | 30% | 30% |
| Zinc carbonate | 2% | 2% | 2% | 2% | 2% | 2% | 2% | 2% | 2% | 2% |
| Zinc gluconate | 1% | 1% | 1% | 1% | 1% | 1% | 1% | 1% | 1% | 1% |
| Caprylic acid | 1% | 1% | 1% | 1% | 1% | 1% | 1% | 1% | 1% | 1% |
| Nonanoic acid | 1% | 1% | 1% | 1% | 1% | 1% | 1% | 1% | 1% | 1% |

[1]COLADET SDC: alkylbenzene sulfonate, coconut amide, and mixed ethoxylated alcohols
[2]COLADET DC-6: anionic-amide blend
[3]COLADET RA: blend of nonionic surfactants
[4]COLADET GBP: ammonium laureth sulfate, disodium cocoamphodiacetate, lauryl glucoside, decyl glucoside, cocamidopropyl betaine.
[5]COLADET KC-40: potassium cocoate
[6]KLUCELL: hydroxypropyl cellulose
[7]KURARY KL-506: polyvinyl alcohol

Examples 21-23

In Examples 21-23, sheet soaps were prepared in accordance with the present invention (Table 4) and physical properties of the resulting sheets were measured (Table 5). Masses of all components were measured in grams (g). Percent weights "%" indicate percent by weight of the total weight of the sheet soap, including all components.

For the dispersion test, sheet soap samples were cut into two 1.5 inch×2 inch specimens (with a weight of about 0.5 g). Then, the specimens were added to a 250 mL clear jar, along with 180 mL of water. The jar was shaken on a laboratory shaker at a speed of 180 strokes/minute. When the sheet soap disappeared in the water, the time, in seconds, was recorded. As shown, the dispersion time of cross-linked samples was longer than non cross-linked samples.

TABLE 4

|  | Example | | |
|---|---|---|---|
|  | 21 | 22 | 23 |
| COLADET SDC[1] | 60% | 58% | 56% |
| KLUCELL[2] | 10% | 10% | 10% |
| KURARAY KL-506[3] | 30% | 30% | 30% |
| Zinc carbonate | 0% | 2% | 4% |

[1]COLADET SDC alkylbenzene sulfonate, coconut amide, and mixed ethoxylated alcohols
[2]KLUCELL hydroxypropyl cellulose
[3]KURARY KL-506 carboxylated polyvinyl alcohol

TABLE 5

|  | Example | | |
|---|---|---|---|
|  | 21 | 22 | 23 |
| Basis weight (g/m$^2$) | 143.6 | 136.2 | 142.1 |
| Caliper (μm) | 205 | 156 | 191 |
| Bulk (cm$^3$/g) | 1.4 | 1.1 | 1.3 |

TABLE 5-continued

|  | Example | | |
|---|---|---|---|
|  | 21 | 22 | 23 |
| Tensile MD (g/inch) | 792 | 644 | 703 |
| Stretch MD (%) | 59.3 | 54.9 | 38.03 |
| Breaking length (cm) | 0.217 | 0.186 | 0.195 |
| Dispersion in water (seconds) | 11 | 17 | 26 |

Samples of sheet soaps (about 0.65 g each) were coated on both sides (about 5% to 6% by weight of each sample) with dimethicone siloxane oil (an emollient) as shown in Table 6. Uncoated sheet soaps were compared. All samples were maintained in a room at 100° F. and 90% relative humidity for 24 hours. Moisture penetration can weaken the sheet soap, which is undesirable. However, when sheet soaps were coated with the emollient, moisture penetration was prevented. This result may be applicable to other emollients, such as non-linear esters, non-linear esters, or short chain fatty acids. The (%) moisture add-on (wt. %) is shown in Table 6. The % moisture add-on was determined by weighing the sheet soap before and after the 24 hour period.

TABLE 6

| | Example | | |
|---|---|---|---|
| | 21 | 22 | 23 |
| Uncoated | 8.9% | 8.3% | 8.7% |
| Dimethicone siloxane oil | 7.6% | 0% | 0% |

The foregoing is considered as illustrative only of the principles of the invention. Further, various modifications may be made of the invention without departing from the scope thereof, and it is desired, therefore, that only such limitations shall be placed thereon as are imposed by the prior art and which are set forth in the appended claims.

With respect to the above description, it is to be realized that the optimum proportional relationships for the parts of the invention, to include variations in components, concentration, shape, form, function, and manner of manufacture, and use, are deemed readily apparent and obvious to one skilled in the art, and all equivalent relationships to those illustrated in the specification are intended to be encompassed by the present invention.

Therefore, the foregoing is considered as illustrative only of the principles of the invention. Further, various modifications may be made of the invention without departing from the scope thereof, and it is desired, therefore, that only such limitations shall be placed thereon as are imposed by the prior art and which are set forth in the appended claims.

What is claimed is:

1. A foam soap delivery system comprising:
   a) a paperboard core comprising a first distal end and a second distal end;
   b) a plurality of sheets of a paper or a tissue wound around the paperboard core;
   c) a dispenser removably disposed within the paperboard core;
   d) a water-soluble sheet soap disposed within the dispenser, the sheet soap being dissolvable in water to form a foamable solution, the sheet soap having a bending resistance in a range between about 1 milligram-force (mgf) and about 50 mgf as measured by Technical Association of the Pulp and Paper Industry (TAPPI) test method T 543 om-11;
   e) the sheet soap comprising a contact product of polyvinyl alcohol, at least one film-forming material, an ionic cross-linker composition, and a surfactant composition, the polyvinyl alcohol, the at least one film-forming material, and the ionic cross-linker composition defining a film-forming composition, the film-forming composition being present in a range between about 20% and about 50% by weight of the total weight of the sheet soap, the polyvinyl alcohol being present in the film-forming composition in a range between about 5% and about 60% by weight of the total weight of the sheet soap, and the ionic cross-linker composition being present in the film-forming composition in a range between about 1% to about 10% by weight of the total weight of the sheet soap; and
   f) the dispenser discharging a foam upon stimulation by a user when water is present within the dispenser.

2. The foam soap delivery system of claim 1, wherein the dispenser comprises a container and a pump removably and sealably engaging the container.

3. The foam soap delivery system of claim 2, wherein the pump is a hand-actuatable pump.

4. The foam soap delivery system of claim 2, wherein:
   the sheet soap is dissolvable in the water to produce a foamable solution; and
   the hand-actuatable pump mixes air with the foamable solution to produce and discharge the foam upon actuation by the user.

5. The foam soap delivery system of claim 2, wherein:
   the sheet soap is dissolvable in water to produce a foamable solution; and
   the pump is a motion-actuated pump having a sensor which senses a motion of the user and mixes air with the foamable solution to produce and discharge the foam upon sensing the motion of the user.

6. The foam soap delivery system of claim 1, wherein the dispenser comprises a container and a cap removably and sealably engaging the container, the cap comprising a nozzle, a spout, or an outlet.

7. The foam soap delivery system of claim 1, further comprising a hanger disposed on the dispenser, the hanger having at least one hook extending outwardly in either a radial or an axial direction with respect to the hanger for engaging one of the distal ends of the paperboard core.

8. The foam soap delivery system of claim 1, wherein the at least one film-forming material of the water-soluble sheet soap is a vinyl polymer, a cellulose-based polymer, a starch, a polysaccharide, a gum, a polyquaternium polymer, a polyhydroxy acid polymer, or any combination thereof.

9. The foam soap delivery system of claim 1, wherein the at least one film-forming material of the water-soluble sheet soap is polyvinyl pyrrolidone, hydroxypropyl cellulose, (hydroxypropylcellulose)polyethylene glycol, hydroxyethyl cellulose, hydroxypropyl cellulose gelatin, carboxymethyl cellulose, hydroxypropyl starch phosphate, aluminum starch octenyl succinate, xantham gum, guar gum, locust bean gum, karaya gum, tragacanth gum, *acacia* gum, arabic gum, amylase, dextrin, pectin, chitin, chitosan, pullulan, gluten, levan, sodium alginate, agar, align, carrageenan, gellan, furcellaran, elsinan, collagen, soy protein isolate, whey protein isolate, casein, polyacrylic acid polymer, methylmethacylate copolymer, carboxyvinyl polymer, poly(2-ethyl-2-oxazoline), or any combination thereof.

10. The foam soap delivery system of claim 1, wherein the film-forming material of the water-soluble sheet soap is hydroxypropylmethyl cellulose.

11. The foam soap delivery system of claim 1, wherein the ionic cross-linker composition of the water-soluble sheet soap is a polyvalent amine, a polyvalent metal hydroxide, a polyvalent metal oxide, a polyvalent metal inorganic salt, a polyvalent metal organic salt, an alkali earth metal salt, or any combination thereof.

12. The foam soap delivery system of claim 1, wherein the ionic cross-linker composition of the water-soluble sheet soap is aluminum hydroxide, calcium hydroxide, magnesium hydroxide, zinc hydroxide, aluminum oxide, calcium oxide, zirconium oxide, magnesium oxide, lead oxide, zinc oxide, aluminum sulfate, aluminum potassium sulfate, aluminum carbonate, aluminum chloride, calcium sulfate, calcium carbonate, calcium chloride, magnesium sulfate, magnesium carbonate, magnesium chloride, zinc sulfate, zinc carbonate, zinc gluconate, zinc lactate, zinc chloride, aluminum methasilicate, aluminum acetate, calcium acetate, magnesium acetate, zinc acetate, aluminum glycinate, ammonium zirconium carbonate, potassium zirconium acetate, zirconium stearate, or any combination thereof.

13. The foam soap delivery system of claim 1, wherein the ionic cross-linker composition of the water-soluble sheet soap is aluminum hydroxide, calcium hydroxide, magnesium hydroxide, zinc hydroxide, aluminum sulfate, aluminum potassium sulfate, aluminum carbonate, aluminum chloride, calcium sulfate, calcium carbonate, calcium chloride, magnesium sulfate, magnesium carbonate, magnesium chloride, zinc sulfate, zinc carbonate, zinc gluconate, zinc lactate, zinc chloride, aluminum methasilicate, aluminum acetate, calcium acetate, magnesium acetate, zinc acetate, aluminum glycinate, ammonium zirconium carbonate, potassium zirconium acetate, zirconium stearate, or any combination thereof.

14. The foam soap delivery system of claim 1, wherein surfactant composition of the water-soluble sheet soap is in a range between about 40% and about 50% by weight of the total weight of the sheet soap.

15. The foam soap delivery system of claim 1, wherein the surfactant composition of the water-soluble sheet soap is a nonionic surfactant, an anionic surfactant, a cationic surfactant, an amphoteric surfactant, or any combination thereof.

16. The foam soap delivery system of claim 1, the water-soluble sheet soap further comprising a filler in a range between about 1% and about 2% by weight of the total weight of the sheet soap.

17. A foam soap delivery system comprising:
a) a paperboard core comprising a first distal end and a second distal end;
b) a plurality of sheets of a paper or a tissue wound around the paperboard core;
c) a dispenser removably disposed within the paperboard core;
d) a water-soluble sheet soap disposed within the dispenser, the sheet soap being dissolvable in water to form a foamable solution, the sheet soap having a bending resistance in a range between about 1 milligram-force (mgf) and about 50 mgf as measured by TAPPI test method T 543 om-11;
e) the sheet soap comprising a contact product of polyvinyl alcohol, at least one film-forming material, an ionic cross-linker composition, a surfactant composition, and an antimicrobial composition, the polyvinyl alcohol, the at least one film-forming material, and the ionic cross-linker composition defining a film-forming composition, the film-forming composition being present in a range between about 10% and about 40% by weight of the total weight of the sheet soap, the polyvinyl alcohol being present in the film-forming composition in a range between about 10% and about 55% by weight of the total weight of the sheet soap, and the ionic cross-linker composition being present in the film-forming composition in a range between about 1% and about 10% by weight of the total weight of the sheet soap; and
f) the dispenser discharging a foam upon stimulation by a user when water is present within the dispenser.

18. The foam soap delivery system of claim 17, wherein the dispenser comprises a container and a pump removably and sealably engaging the container.

19. The foam soap delivery system of claim 18, wherein the pump is a hand-actuatable pump.

20. The foam soap delivery system of claim 18, wherein:
the sheet soap is dissolvable in water to produce a foamable solution; and
the hand-actuatable pump mixes air with the foamable solution to produce and discharge the foam upon actuation by the user.

21. The foam soap delivery system of claim 18, wherein:
the sheet soap is dissolvable in water to produce a foamable solution; and
the pump is a motion-actuated pump having a sensor which senses a motion of the user and mixes air with the foamable solution to produce and discharge the foam upon sensing the motion of the user.

22. The foam soap delivery system of claim 17, wherein the dispenser comprises a container and a cap removably and sealably engaging the container, the cap comprising a nozzle, a spout, or an outlet.

23. The foam soap delivery system of claim 17, further comprising a hanger disposed on the dispenser, the hanger having at least one hook extending outwardly in either a radial or an axial direction with respect to the hanger for engaging one of the distal ends of the paperboard core.

24. The foam soap delivery system of claim 17, wherein the at least one film-forming material of the water-soluble sheet soap is a vinyl polymer, a cellulose-based polymer, a starch, a polysaccharide, a gum, a polyquaternium polymer, a polyhydroxy acid polymer, or any combination thereof.

25. The foam soap delivery system of claim 17, wherein the at least one film-forming material of the water-soluble sheet soap is polyvinyl pyrrolidone, hydroxypropyl cellulose, (hydroxypropylcellulose)polyethylene glycol, hydroxyethyl cellulose, hydroxypropyl cellulose gelatin, carboxymethyl cellulose, hydroxypropyl starch phosphate, aluminum starch octenyl succinate, xantham gum, guar gum, locust bean gum, karaya gum, tragacanth gum, *acacia* gum, arabic gum, amylase, dextrin, pectin, chitin, chitosan, pullulan, gluten, levan, sodium alginate, agar, align, carrageenan, gellan, furcellaran, elsinan, collagen, soy protein isolate, whey protein isolate, casein, polyacrylic acid polymer, methylmethacylate copolymer, carboxyvinyl polymer, poly(2-ethyl-2-oxazoline), or any combination thereof.

26. The foam soap delivery system of claim 17, wherein the at least one film-forming material of the water-soluble sheet soap is hydroxypropylmethyl cellulose.

27. The foam soap delivery system of claim 17, wherein the ionic cross-linker composition of the water-soluble sheet soap is a polyvalent amine, a polyvalent metal hydroxide, a polyvalent metal oxide, a polyvalent metal inorganic salt, a polyvalent metal organic salt, an alkali earth metal salt, or any combination thereof.

28. The foam soap delivery system of claim 17, wherein the ionic cross-linker composition of the water-soluble sheet soap is aluminum hydroxide, calcium hydroxide, magnesium hydroxide, zinc hydroxide, aluminum oxide, calcium oxide, zirconium oxide, magnesium oxide, lead oxide, zinc oxide, aluminum sulfate, aluminum potassium sulfate, aluminum carbonate, aluminum chloride, calcium sulfate, calcium carbonate, calcium chloride, magnesium sulfate, magnesium carbonate, magnesium chloride, zinc sulfate, zinc carbonate, zinc gluconate, zinc lactate, zinc chloride, aluminum methasilicate, aluminum acetate, calcium acetate, magnesium acetate, zinc acetate, aluminum glycinate, ammonium zirconium carbonate, potassium zirconium acetate, zirconium stearate, or any combination thereof.

29. The foam soap delivery system of claim 17, wherein the ionic cross-linker composition of the water-soluble sheet soap is aluminum hydroxide, calcium hydroxide, magnesium hydroxide, zinc hydroxide, aluminum sulfate, aluminum potassium sulfate, aluminum carbonate, aluminum chloride, calcium sulfate, calcium carbonate, calcium chloride, magnesium sulfate, magnesium carbonate, magnesium chloride, zinc sulfate, zinc carbonate, zinc gluconate, zinc lactate, zinc chloride, aluminum methasilicate, aluminum acetate, calcium acetate, magnesium acetate, zinc acetate, aluminum glycinate, ammonium zirconium carbonate, potassium zirconium acetate, zirconium stearate, or any combination thereof.

30. The foam soap delivery system of claim 17, wherein the surfactant composition of the water-soluble sheet soap is a nonionic surfactant, an anionic surfactant, a cationic surfactant, an amphoteric surfactant, or any combination thereof.

31. The foam soap delivery system of claim 17, wherein the surfactant composition of the water-soluble sheet soap is in a range between about 40% and about 60% by weight of the total weight of the sheet soap.

32. The foam soap delivery system of claim 17, the water-soluble sheet soap further comprising a filler in a range between about 1% and about 2% by weight of the total weight of the sheet soap.

33. The foam soap delivery system of claim 17, wherein the antimicrobial composition of the water-soluble sheet soap comprises a natural antimicrobial of vegetal origin or animal origin.

34. The foam soap delivery system of claim 17, wherein the antimicrobial composition of the water-soluble sheet soap is in a range between about 1% and about 5% by weight of the total weight of the sheet soap.

35. The foam soap delivery system of claim 17, the water-soluble sheet soap further comprising an emollient in a range between about 1% and about 5% by weight of the total weight of the sheet soap.

36. The foam soap delivery system of claim 17, the water-soluble sheet soap further comprising at least one additive in a range between about 1% and about 2% by weight of the total weight of the sheet soap.

37. The foam soap delivery system of claim 17, the water-soluble sheet soap further comprising at least one additive, wherein the additive is an essential oil, a humectant, an antioxidant, a buffer, a fragrance, a colorant, or any combination thereof.

38. A foam soap delivery system comprising:
a) a paperboard core comprising a first distal end and a second distal end;
b) a plurality of sheets of a paper or a tissue wound around the paperboard core;
c) a dispenser removably disposed within the paperboard core;
d) a water-soluble sheet soap disposed within the dispenser, the sheet soap being dissolvable in water to form a foamable solution, the sheet soap having a bending resistance in a range between about 1 milligram-force (mgf) and about 50 mgf as measured by TAPPI test method T 543 om-11;
e) the sheet soap comprising a contact product of polyvinyl alcohol, at least one film-forming material, an ionic cross-linker composition, and a surfactant composition, the polyvinyl alcohol, the at least one film-forming material, and the ionic cross-linker composition defining a film-forming composition, the film-forming composition being present in a range between about 20% and about 50% by weight of the total weight of the sheet soap, the polyvinyl alcohol being present in the film-forming composition in a range between about 5% and about 60% by weight of the total weight of the sheet soap, the ionic cross-linker composition being present in the film-forming composition in a range between about 1% and about 10% by weight of the total weight of the sheet soap, and the surfactant composition being present in a range between about 50% and about 60% by weight of the total weight of the sheet soap; and
f) the dispenser discharging a foam upon stimulation by a user when water is present within the dispenser.

39. The foam soap delivery system of claim 38, wherein the dispenser comprises a container and a pump removably and sealably engaging the container.

40. The foam soap delivery system of claim 39, wherein the pump is a hand-actuatable pump.

41. The foam soap delivery system of claim 39, wherein:
the sheet soap is dissolvable in water to produce a foamable solution; and
the hand-actuatable pump mixes air with the foamable solution to produce and discharge the foam upon actuation by the user.

42. The foam soap delivery system of claim 39, wherein:
the sheet soap is dissolvable in water to produce a foamable solution; and
the pump is a motion-actuated pump having a sensor which senses a motion of the user and mixes air with the foamable solution to produce and discharge the foam upon sensing the motion of the user.

43. The foam soap delivery system of claim 38, wherein the dispenser comprises a container and a cap removably and sealably engaging the container, the cap comprising a nozzle, a spout, or an outlet.

44. The foam soap delivery system of claim 38, further comprising a hanger disposed on the dispenser, the hanger having at least one hook extending outwardly in either a radial or an axial direction with respect to the hanger for engaging one of the distal ends of the paperboard core.

45. The foam soap delivery system of claim 38, wherein the at least one film-forming material of the water-soluble sheet soap is a vinyl polymer, a cellulose-based polymer, a starch, a polysaccharide, a gum, a polyquaternium polymer, a polyhydroxy acid polymer, or any combination thereof.

46. The foam soap delivery system of claim 38, wherein the at least one film-forming material of the water-soluble sheet soap is polyvinyl pyrrolidone, hydroxypropyl cellulose, (hydroxypropylcellulose)polyethylene glycol, hydroxyethyl cellulose, hydroxypropyl cellulose gelatin, carboxymethyl cellulose, hydroxypropyl starch phosphate, aluminum starch octenyl succinate, xantham gum, guar gum, locust bean gum, karaya gum, tragacanth gum, *acacia* gum, arabic gum, amylase, dextrin, pectin, chitin, chitosan, pullulan, gluten, levan, sodium alginate, agar, align, carrageenan, gellan, furcellaran, elsinan, collagen, soy protein isolate, whey protein isolate, casein, polyacrylic acid polymer, methylmethacylate copolymer, carboxyvinyl polymer, poly(2-ethyl-2-oxazoline), or any combination thereof.

47. The foam soap delivery system of claim 38, wherein the film-forming material of the water-soluble sheet soap is hydroxypropylmethyl cellulose.

48. The foam soap delivery system of claim 38, wherein the ionic cross-linker composition of the water-soluble sheet soap is a polyvalent amine, a polyvalent metal hydroxide, a polyvalent metal oxide, a polyvalent metal inorganic salt, a polyvalent metal organic salt, an alkali earth metal salt, or any combination thereof.

49. The foam soap delivery system of claim 38, wherein the ionic cross-linker composition of the water-soluble sheet soap is aluminum hydroxide, calcium hydroxide, magnesium hydroxide, zinc hydroxide, aluminum oxide, calcium oxide, zirconium oxide, magnesium oxide, lead oxide, zinc oxide, aluminum sulfate, aluminum potassium sulfate, aluminum carbonate, aluminum chloride, calcium sulfate, calcium carbonate, calcium chloride, magnesium sulfate, magnesium carbonate, magnesium chloride, zinc sulfate, zinc carbonate, zinc gluconate, zinc lactate, zinc chloride, aluminum methasilicate, aluminum acetate, calcium acetate, magnesium acetate, zinc acetate, aluminum glycinate, ammonium zirconium carbonate, potassium zirconium acetate, zirconium stearate, or any combination thereof.

50. The foam soap delivery system of claim 38, wherein the ionic cross-linker composition of the water-soluble sheet soap is aluminum hydroxide, calcium hydroxide, magnesium hydroxide, zinc hydroxide, aluminum sulfate, aluminum potassium sulfate, aluminum carbonate, aluminum chloride, calcium sulfate, calcium carbonate, calcium chloride, magnesium sulfate, magnesium carbonate, magnesium chloride, zinc sulfate, zinc carbonate, zinc gluconate, zinc lactate, zinc chloride, aluminum methasilicate, aluminum acetate, calcium acetate, magnesium acetate, zinc acetate, aluminum glycinate, ammonium zirconium carbonate, potassium zirconium acetate, zirconium stearate, or any combination thereof or any combination thereof.

51. The foam soap delivery system of claim 38, wherein the surfactant composition of the water-soluble sheet soap comprise is a nonionic surfactant, an anionic surfactant, a cationic surfactant, an amphoteric surfactant, or any combination thereof.

52. The foam soap delivery system of claim 38, the water-soluble sheet soap further comprising a filler in a range between about 1% and about 2% by weight of the total weight of the sheet soap.

53. A foam soap delivery system for dispensing a metered amount of foam, the foam soap delivery system comprising:
    a) a paperboard core comprising a first distal end and a second distal end;
    b) a plurality of sheets of a paper or a tissue wound around the paperboard core;
    c) a dispenser removably disposed within the paperboard core;
    d) a water-soluble sheet soap disposed within the dispenser, the sheet soap being dissolvable in water to form a foamable solution, the sheet soap having a bending resistance in a range between about 1 milligram-force (mgf) and about 50 mgf as measured by TAPPI test method T 543 om-11;
    e) the sheet soap comprising a contact product of polyvinyl alcohol, at least one film-forming material, an ionic cross-linker composition, and a surfactant composition, the polyvinyl alcohol, the at least one film-forming material, and the ionic cross-linker composition defining a film-forming composition, the film-forming composition being present in a range between about 20% and about 50% by weight of the total weight of the sheet soap, the polyvinyl alcohol being present in the film-forming composition in a range between about 5% and about 60% by weight of the total weight of the sheet soap, and the ionic cross-linker composition being present in the film-forming composition in a range between about 1% and about 10% by weight of the total weight of the sheet soap; and
    f) the dispenser discharging the metered amount of foam upon stimulation by a user when sufficient water is present within the dispenser to produce an effective concentration of the foamable solution, the effective concentration of the foamable solution being defined as at least 1 milligrams of sheet soap per 1 milliliter of water.

54. The foam soap delivery system of claim 53, wherein the dispenser comprises a container and a pump removably and sealably engaging the container.

55. The foam soap delivery system of claim 54, wherein the pump is a hand-actuatable pump.

56. The foam soap delivery system of claim 54, wherein:
    the sheet soap is dissolvable in water to produce a foamable solution; and
    the hand-actuatable pump mixes air with the foamable solution to produce and discharge the foam upon actuation by the user.

57. The foam soap delivery system of claim 54, wherein:
    the sheet soap is dissolvable in water to produce a foamable solution; and
    the pump is a motion-actuated pump having a sensor which senses a motion of the user and mixes air with the foamable solution to produce and discharge the foam upon sensing the motion of the user.

58. The foam soap delivery system of claim 53, wherein the dispenser comprises a container and a cap removably and sealably engaging the container, the cap comprising a nozzle, a spout, or an outlet.

59. The foam soap delivery system of claim 53, further comprising a hanger disposed on the dispenser, the hanger having at least one hook extending outwardly in either a radial or an axial direction with respect to the hanger for engaging one of the distal ends of the paperboard core.

60. The foam soap delivery system of claim 53, wherein the at least one film-forming material of the water-soluble sheet soap is a vinyl polymer, a cellulose-based polymer, a starch, a polysaccharide, a gum, a polyquaternium polymer, a polyhydroxy acid polymer, or any combination thereof.

61. The foam soap delivery system of claim 53, wherein the at least one film-forming material of the water-soluble sheet soap is polyvinyl pyrrolidone, hydroxypropyl cellulose, (hydroxypropylcellulose)polyethylene glycol, hydroxyethyl cellulose, hydroxypropyl cellulose gelatin, carboxymethyl cellulose, hydroxypropyl starch phosphate, aluminum starch octenyl succinate, xantham gum, guar gum, locust bean gum, karaya gum, tragacanth gum, *acacia* gum, arabic gum, amylase, dextrin, pectin, chitin, chitosan, pullulan, gluten, levan, sodium alginate, agar, align, carrageenan, gellan, furcellaran, elsinan, collagen, soy protein isolate, whey protein isolate, casein, polyacrylic acid polymer, methylmethacylate copolymer, carboxyvinyl polymer, poly(2-ethyl-2-oxazoline), or any combination thereof.

62. The foam soap delivery system of claim 53, wherein the at least one film-forming material of the water-soluble sheet soap is hydroxypropylmethyl cellulose.

63. The foam soap delivery system of claim 53, wherein the ionic cross-linker composition of the water-soluble sheet soap comprises a polyvalent amine, a polyvalent metal hydroxide, a polyvalent metal oxide, a polyvalent metal inorganic salt, a polyvalent metal organic salt, an alkali earth metal salt, or any combination thereof.

64. The foam soap delivery system of claim 53, wherein the ionic cross-linker composition of the water-soluble sheet soap comprise is aluminum hydroxide, calcium hydroxide, magnesium hydroxide, zinc hydroxide, aluminum oxide, calcium oxide, zirconium oxide, magnesium oxide, lead oxide, zinc oxide, aluminum sulfate, aluminum potassium sulfate, aluminum carbonate, aluminum chloride, calcium sulfate, calcium carbonate, calcium chloride, magnesium sulfate, magnesium carbonate, magnesium chloride, zinc sulfate, zinc carbonate, zinc gluconate, zinc lactate, zinc chloride, aluminum methasilicate, aluminum acetate, calcium acetate, magnesium acetate, zinc acetate, aluminum glycinate, ammonium zirconium carbonate, potassium zirconium acetate, zirconium stearate, or any combination thereof.

65. The foam soap delivery system of claim 53, wherein the ionic cross-linker composition of the water-soluble sheet soap is aluminum hydroxide, calcium hydroxide, magnesium hydroxide, zinc hydroxide, aluminum sulfate, aluminum potassium sulfate, aluminum carbonate, aluminum chloride, calcium sulfate, calcium carbonate, calcium chloride, magnesium sulfate, magnesium carbonate, magnesium chloride, zinc sulfate, zinc carbonate, zinc gluconate, zinc lactate, zinc chloride, aluminum methasilicate, aluminum acetate, calcium acetate, magnesium acetate, zinc acetate, aluminum glycinate, ammonium zirconium carbonate, potassium zirconium acetate, zirconium stearate, or any combination thereof.

66. The foam soap delivery system of claim 53, wherein surfactant composition of the water-soluble sheet soap is in a range between about 40% and about 60% by weight of the total weight of the sheet soap.

67. The foam soap delivery system of claim 53, wherein the surfactant composition of the water-soluble sheet soap is a nonionic surfactant, an anionic surfactant, a cationic surfactant, an amphoteric surfactant, or any combination thereof.

68. The foam soap delivery system of claim 53, the water-soluble sheet soap further comprising a filler in a range between about 1% and about 2% by weight of the total weight of the sheet soap.

* * * * *